United States Patent [19]
Burns et al.

[11] Patent Number: 5,663,154
[45] Date of Patent: Sep. 2, 1997

[54] 2',3'-DIDEOXY-3'-FLUORO-PURINE RIBONUCLEOSIDES

[75] Inventors: Charlene Louise Burns, Durham; George Walter Koszalka; Thomas Anthony Krenitsky, both of Chapel Hill, all of N.C.

[73] Assignee: Glaxo Wellcome Inc., Research Triangle Park, N.C.

[21] Appl. No.: 256,310

[22] PCT Filed: Jan. 5, 1993

[86] PCT No.: PCT/GB93/00004

§ 371 Date: Jun. 30, 1994

§ 102(e) Date: Jun. 30, 1994

[87] PCT Pub. No.: WO93/14103

PCT Pub. Date: Jul. 22, 1993

[30]   Foreign Application Priority Data

Jan. 6, 1992 [GB] United Kingdom ................. 9200149
Sep. 25, 1992 [GB] United Kingdom ................. 9220317

[51] Int. Cl.$^6$ ........................ A61K 31/70; C07H 19/173
[52] U.S. Cl. .......................... 514/45; 514/46; 536/27.14
[58] Field of Search .................. 514/45, 46; 536/27.14

[56]   References Cited

U.S. PATENT DOCUMENTS 4,381,344  4/1983  Rideout et al. ............................ 435/87
4,963,662  10/1990 Matthes et al. ............................ 514/45

FOREIGN PATENT DOCUMENTS 254 268   1/1988  European Pat. Off. .
317 128   5/1989  European Pat. Off. .
409 227   1/1991  European Pat. Off. .
0129390   1/1989  Japan .

OTHER PUBLICATIONS

Chemical Abstracts, vol. 115; p. 975, Abstr. No. 183751, 1991, Motawia et al. Liebigs Ann. Chem. 9: 879–883, 1991).

Korba et al., "A Cell Culture Assay for Compounds Which Inhibit Hepatitis B Virus Replication," Antiviral Research, 15, 217–228 (1991) month not available.

Robinson, "Fields Virology," Edited by Fields et al., vol. 2, (1990) Raven Press, New York, Chapters 76 & 77 month not available.

Averett, "Anti–HIV Compound Assessment by Two Novel High Capacity Assays," J. Virol. Methods, 23, 263–276 (1989) month not available.

Herdewijn et al., "Synthesis and Anti–HIV Activity of Different Sugar–Modified Pyrimidine and Purine Nucleosides," J. Med. Chem., 31, 2040–2048 (1988) month not available.

Sells et al., "Replicative Intermediates of Hepatitis B Virus in HepG2 Cells That Produce Infectious Virions," J. Virol., 62(8),2836 (1988) month not available.

Sells et al., "Production of Hepatitis B Virus Particles in Hep G2 Cells Transfected With Cloned Hepatitis B Virus DNA," Proc. Natl. Acad. Sci. USA, 84, 1005–1009 (1987) month not available.

Tyle, "Iontophoretic Devices for Drug Delivery," Pharmaceutical Research, 3(6), 318–326 (1986) month not available.

Krenitsky et al., "Purine Nucleoside Synthesis, An Efficient Method Employing Nucleoside Phosphorylases," Biochemistry, 20, 3615–3621 (1981) month not available.

Cardinaud, "Nucleoside Deoxyribosyltransferase From Lactobacillus Helveticus," Methods in Enzymology, 51,446–455 (1978) month not available.

Southern, "Detection of Specific Sequences Among DNA Fragments Separated by Gel Electrophoresis," J. Mol. Bio., 98, 503–517 (1975) month not available.

Kowollick et al, "Ein Neuer Zugang Zu 1–(2, 3–Didesoxy–3–fluor–β–d–ribofuranosyl)–pyrimidinen," J. Prakt. Chem, 315(5), 895–900 (1973) month not available.

Etzold et al., "Nucleoside Von Fluorzuckern–VI$^1$," Tetrahedron, 27, 2463–2472 (1971) month not available.

Montgomery et al., "Synthesis of Potential Anticancer Agents. XXVI. The Alkylation of 6–Chloropurine," J. Amer. Chem. Soc., 83, 630–635 (1961) month not available.

Robins et al., "Potential Purine Antagonists. IV. Synthesis of Some 9–Methyl–6–substituted–purines," J. Amer. Chem. Soc., 79. 490–494 (1957) month not available.

*Primary Examiner*—Gary L. Kunz
*Attorney, Agent, or Firm*—Karen L. Prus

[57]   ABSTRACT

2',3'-Dideoxy-3'-fluoro-(B-D-ribofuranosyl) purine nucleosides possessing the ability to inhibit hepatitis B and HIV viral infections.

11 Claims, No Drawings

2',3'-DIDEOXY-3'-FLUORO-PURINE RIBONUCLEOSIDES

This case is a 371 of PCT/GB 93/00004 filed Jan. 5, 1993.

The present invention relates to novel 2',3'-dideoxy-3'-fluoro-purine nucleoside compounds, physiologically functional derivatives thereof, processes for their preparation, pharmaceutical formulations containing them and the use of such analogues and derivative compounds in therapy, particularly the treatment or prophylaxis of viral infections.

One group of viruses which has assumed a particular importance is the retroviruses. Retroviruses form a subgroup of RNA viruses which, in order to replicate, must first 'reverse transcribe' the RNA of their genome into DNA ('transcription' conventionally describes the synthesis of RNA from DNA). Once in the form of DNA, the viral genome may be incorporated into the host cell genome, allowing it to take advantage of the host cell's transcription/translation machinery for the purposes of replication. Once incorporated, the viral DNA is virtually indistinguishable from the host's DNA and, in this state, the virus may persist for the life of the cell.

A species of retrovirus, Human Immunodeficiency Virus (HIV), has been reproducibly isolated from humans with Acquired Immune Deficiency Syndrome (AIDS) or with the symptoms that frequently precede AIDS. AIDS is an immunosuppressive or immunodestructive disease that predisposes subjects to fatal opportunistic infections. Characteristically, AIDS is associated with a progressive depletion of T-cells, especially the helper-inducer subset bearing the $OKT^4$ surface marker. HIV is cytopathic and appears to preferentially infect and destroy T-cells bearing the $OKT^4$ marker and it is now generally recognised that HIV is the etiological agent of AIDS.

Since the discovery that HIV is the etiological agent of AIDS, numerous proposals have been made for anti-HIV chemotherapeutic agents that may be effective in treating AIDS. Thus, for example, European Patent Specification No. 196185 describes 3'-azido-3'-deoxythymidine (which has the approved name zidovudine), its pharmaceutically acceptable derivatives and their use in the treatment of human retrovirus infections including AIDS and associated clinical conditions. Other nucleoside derivatives which have been suggested for the treatment of HIV infections include the 3'-fluoronucleosides described in European Patent No. 0 254 268. European Patent Specification No. 0 317 128 discloses certain 3'-fluoro-purine and pyrimidine nucleoside analogues having anti-HIV activity.

Another group of viral pathogens of major consequence worldwide are the hepatitis viruses, in particular hepatitis B virus (HBV). HBV is most common in Asian countries and prevalent in sub-Saharan Africa. The virus is etiologically associated with primary hepatocellular carcinoma and is thought to cause 80% of the world's liver cancer. In the United States more than ten thousand people are hospitalised for HBV-related illness each year and an average of 250 die with fulminant disease. The United States currently contains an estimated pool of 500,000–1 million infectious carriers. Chronic active hepatitis will develop in over 25% of carriers and often progresses to cirrhosis. It is estimated that 5000 people die from HBV related cirrhosis each year in the USA and that perhaps 1000 die from HBV-related liver cancer. Thus, there is a great need for effective antiviral agents, both to control the chronic infection and to reduce progression to hepatocellular carcinoma.

Clinical effects of infection with HBV range from headache to fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above. In "Fields Virology" (Volume 2 Ed., Fields et al (1990) Raven, New York), Chapters 76 and 77 describe the etiology of viral hepatitis infections.

The anti-HIV and -HBV activity of the compound 2',3'-dideoxy-3'-fluoroadenine and 2',3'-dideoxy-3'-fluoroguanosine is described in International Patent Specification No. WO 88/00050.

We have now identified certain 2',3'-dideoxy-3'-fluoropurine nucleoside analogues and salts, esters or physiologically functional derivatives thereof, which have unexpectedly been found suitable for use as antiviral agents.

European Patent Specifications No. EP 0 317 128 and EP 0 409 227 disclose certain 2',3'-dideoxy-3'-fluoro-purinenucleosides. However, there is no disclosure of the compounds of formula (I) infra.

According to one aspect, the present invention provides a compound of formula (I)

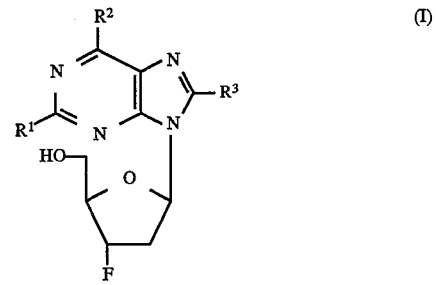

wherein:
$R^1$ represents hydrogen, amino, or halogen;
$R^2$ represents
  -halogen;
  —$NR^4R^5$ wherein $R^4$ and $R^5$, which may be the same or different, each represent hydrogen; $C_{1-4}$hydroxyalkyl; $C_{1-6}$alkyl; $C_{3-6}$cycloalkyl; $C_{2-6}$alkenyl; $C_{6-10}$aryl; or $C_{6-10}$aryl$C_{1-3}$ alkyl, (where the aryl moiety may be optionally substituted by one or more substituents selected from halogen $C_{1-6}$alkoxy, nitro, cyano, amino and $C_{1-6}$alkyl); or $R^6O$—(Ar)—$(CH_2)$n (where the $R^6$ is $C_{1-6}$alkyl, Ar is $C_{6-10}$aryl and n=0,1,2, or 3); or —$R^4R^5$— together with the N atom to which they are attached form a 3,4,5,6 or 7-membered heterocyclic ring optionally containing, in addition to said nitrogen, one or more other hetero atoms independently selected from O, N and S;
  —$S(=O)_nR^7$, where n is 0, 1, or 2 and $R^7$ represents $C_{1-6}$alkyl; $C_{3-6}$cycloalkyl, $C_{3-6}$cycloalkyl$C_{1-3}$alkyl, $C_{1-4}$alkoxy; $C_{6-10}$aryl, or $C_{6-10}$aryl$C_{1-3}$alkyl, (where the aryl moiety may be optionally substituted by one or more substituents selected from halogen, nitro, cyano, amino, or $C_{1-6}$alkyl, $C_{1-6}$alkoxy); or when n is O, $R^7$ is hydrogen; or
  —$OR^8$, where $R^8$ represents hydrogen, $C_{1-6}$alkyl; $C_{3-6}$cycloalkyl, $C_{3-6}$cycloalkyl$C_{1-3}$alkyl; $C_{6-10}$aryl or $C_{6-10}$aryl$C_{1-3}$alkyl (where the aryl moiety may be optionally substituted by one or more substituents selected from halogen, nitro, cyano, amino, or $C_{1-6}$alkyl, $C_{1-6}$alkoxy); and $R^3$ represents hydrogen, amino, halogen or $C_{1-6}$alkyl; with the proviso that:
(1) when $R^1$ is hydrogen, amino or halogen and $R^3$ is hydrogen, then $R^2$ is not:

(a) —NR$^4$R$^5$ wherein:
   (i) R$^4$ and R$^5$ are both hydrogen;
   (ii) R$^4$ and R$^5$ are both C$_{1-6}$ alkyl;
(b) —OR$^8$ wherein R$^8$ is hydrogen;
(c) —S(=O)$_n$R$^7$ wherein n is O and R$^7$ is hydrogen;
(d) halogen and (2) when R$^1$ is hydrogen or amino and R$^3$ is hydrogen, then R$^2$ is not:
   (a) —NR$^4$R$^5$ wherein:
      (i) R$^4$ is hydrogen and R$^5$ is C$_{3-6}$ cycloalkyl; or
      (ii) —R$^4$R$^5$— together with the N atom to which they are attached form a 5- or 6-membered ring wherein said nitrogen is the only heteroatom; or
   (b) —OR$^8$ wherein R$^8$ is C$_{1-6}$ alkyl or C$_{3-6}$ cycloalkyl;

or a salt, ester or physiologically functional derivative of a compound of formula (I) or a solvate of any thereof.

The compounds of formula (I) supra include compounds of formula (IA)

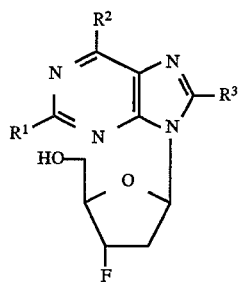

(IA)

wherein

R$^1$ and R$^3$ are as defined above and R$^2$ is any one of the R$^2$ substituents defined above excluding —NR$^4$R$^5$ wherein R$^4$ and R$^5$, which may be the same or different, represents C$_{1-4}$ hydroxyalkyl; subject to the proviso given above for such R$^1$, R$^2$ and R$^3$ groups in relation to formula (I);

or a salt, ester, or physiologically functional derivative of a compound of formula (IA) or a solvate of any thereof.

According to one embodiment the invention provides compounds of formula (IB)

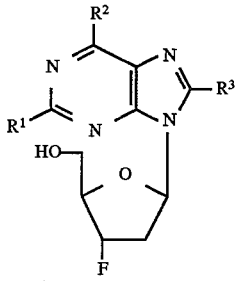

(IB)

wherein R$^1$ and R$^3$ are as hereinbefore defined and R$^2$ represents

-halogen;

—NR$^4$R$^5$ wherein R$^4$ and R$^5$, which may be the same or different, each represent hydrogen; C$_{1-6}$alkyl; C$_{3-6}$cycloalkyl; C$_{1-6}$alkenyl; C$_{6-10}$aryl; or C$_{6-10}$arylC$_{1-3}$ alkyl, (where the aryl moiety may be optionally substituted by one or more substituents selected from halogen C$_{1-6}$alkoxy, nitro, cyano, amino and C$_{1-6}$alkyl); or R$^6$O—(Ar)—(CH$_2$)n (where the R$^6$ is C$_{1-6}$alkyl, Ar is C$_{6-10}$aryl and n=0,1,2, or 3); or —R$^4$R$^5$— together with the N atom to which they are attached form a 4,5,6 or 7-membered heterocyclic ring optionally containing, in addition to said nitrogen, one or more other hereto atoms independently selected from O, N and S;

—S(O)$_n$R$^7$, where n is 0, 1, or 2 and R$^7$ represents C$_{1-6}$alkyl; C$_{3-6}$cycloalkyl; C$_{3-6}$cycloalkyl; C$_{1-4}$alkoxy; C$_{6-10}$aryl or C$_{6-10}$arylC$_{1-3}$alkyl, (where the aryl moiety may be optionally substituted by one or more substituents selected from halogen, nitro, cyano, amino, or C$_{1-6}$alkyl, C$_{1-6}$alkoxy); or —OR$^8$, where R$^8$ represents hydrogen, C$_{1-6}$alkyl; C$_{3-6}$cycloalkyl, C$_{3-6}$cycloalkylC$_{1-3}$alkyl; C$_{6-10}$aryl or C$_{6-10}$arylC$_{1-3}$alkyl (where the aryl moiety may be optionally substituted by one or more substituents selected from halogen, nitro, cyano, amino, or C$_{1-6}$alkyl, C$_{1-6}$alkoxy); and R$^3$ represents hydrogen, amino, halogen or C$_{1-6}$alkyl;

with the proviso that when R$^1$ is hydrogen or amino and R$^3$ is hydrogen, then R$^2$ is not (1) —NR$^4$R$^5$ wherein
   (i) R$^4$ and R$^5$ are both hydrogen;
   (ii) R$^4$ is hydrogen and R$^5$ is C$_{3-6}$cycloalkyl; or
   (iii) —R$^4$R$^5$— together with the N atom to which they are attached form a 5- or 6-membered ring wherein said nitrogen is the only heteroatom; or (2) —OR$^8$ wherein R$^8$ is hydrogen, C$_{1-6}$alkyl, or C$_{3-6}$cycloalkyl;

or a salt, ester or physiologically functional derivative of a compound of formula (IB) or a solvate of any thereof.

As used herein, the term "alkyl" as a group or part of a group means a straight or branched chain alkyl group. Such alkyl groups preferably have 1 to 3 carbon atoms and more preferably are methyl or ethyl, most preferably methyl.

Preferred compounds of formula (I) include those wherein R$^1$ is amino; R$^2$ is —NR$^4$R$^5$ where R$^4$ and R$^5$ are hydrogen, or —OR$^8$ where R$^8$ is hydrogen or C$_{1-6}$alkyl and R$^3$ is amino, or halogen; or salts, esters or physiologically functional derivatives thereof or a solvate of any thereof.

Other preferred compounds of formula (I) include those wherein R$^1$ is hydrogen or amino, R$^3$ is hydrogen and R$^2$ represents:

—NR$^4$R$^5$ wherein R$^4$ and R$^5$ are different from each other and each represent H or C$_{1-6}$alkyl or —R$^4$R$^5$— together with the N atom to which they are attached form a 4-membered heterocyclic ring, which ring is bonded to the purine base via the nitrogen atom;

—OR$^8$, where R$^8$ represents C$_{3-6}$cycloalkylC$_{1-3}$alkyl; C$_{6-10}$arylC$_{1-3}$alkyl; or —S(=O)$_n$R$^7$ where n is O, and R$^7$ represents C$_{1-6}$alkyl;

or a salt, ester or physiologically functional derivative thereof or a solvate of any of the foregoing.

The present invention further includes:

1. Compounds of formula (I) wherein R$^1$ is hydrogen or amino; R$^2$ is —NR$^4$R$^5$ where R$^4$ and R$^5$ are different from each other and each represent H or C$_{1-6}$ alkyl or —S(=O)nR$^7$ where n is O and R$^7$ is C$_{1-6}$alkyl and R$^3$ is hydrogen; or a salt, ester or physiologically functional derivative thereof or a solvate of any thereof. Such compounds are particularly useful in the treatment or prophylaxis of HBV infections.

Preferred compounds include 2-amino-9-(2,3-dideoxy-3-fluoro-β-D-erythro-pentofuranosyl-6-(propylamino)-9H-purine; 9-(2,3-dideoxy-3-fluoro-β-D-erythro-pentofuranosyl)-6-(methylamino)-9H-purine; 2-amino-9-(2, 3-dideoxy-3-fluoro-β-D-erythro-pentofuranosyl)-6-methylmercapto-9-purine; 2-amino-9-(2,3-dideoxy-3- fluoro-β-D-erythro-pentofuranosyl)-6-methylamino-9H-purine and salts, esters and physiologically functional derivatives thereof or a solvate of any of the foregoing.

2. Compounds of formula (I) wherein $R^1$ is amino; $R^2$ is —$NR^4R^5$ wherein $R^4$ and $R^5$ together with the N atom to which they are attached form a 4-membered heterocyclic ring, which ring is bonded to the purine base via the nitrogen atom or —$OR^8$ where $R^8$ represents $C_{3-6}$cycloalkyl$C_{1-3}$alkyl or $C_{6-10}$aryl$C_{1-3}$alkyl and $R^3$ is hydrogen; or a salt, ester or physiologically functional derivative thereof or a solvate of any of the foregoing. Such compounds are particularly useful in the treatment or prophylaxis of HBV and HIV infections.

Preferred compounds include 2-amino-6-(cyclopropylmethoxy)-9-(2,3-dideoxy-3-fluoro-β-D-erythro-pentofuranosyl)-9H-purine, 2-amino-6-benzyloxy-9-(2,3-dideoxy-3-fluoro-β-D-erythro-pentofuranosyl)-9H-purine, 2-amino-6-azetidinyl-9-(2,3-dideoxy-3-fluoro-β-D-erythro-pentofuranosyl)-9H-purine and salts, esters and physiologically functional derivatives thereof or a solvate of any thereof.

The present invention also provides those compounds of formula (I) above wherein $R^1$ is amino, $R^2$ is dimethylamino, ethylmethylamino, methylpropylamino or a chloro atom and $R^3$ is hydrogen; (hereinafter referred to as compounds of formula IC); or a salt, ester or physiologically functional derivatives thereof or a solvate of any of the foregoing.

The compounds of formula (IC) may be named as follows:

2-amino-9-(2,3-dideoxy-3-fluoro-β-D-erythro-pentofuranosyl)-6-(dimethylamino)-9H-purine;

2-amino-9-(2,3-dideoxy-3-fluoro-β-D-erythro-pentofuranosyl)-6-(ethylmethylamino)-9H-purine;

2-amino-9-(2,3-dideoxy-3-fluoro-β-D-erythro-pentofuranosyl)-6-methylpropylamino)-9H-purine;

2-amino-6-chloro-9-(2,3-dideoxy-3-fluoro-β-D-erythro-pentofuranosyl);

or a salt, ester or a physiologically functional derivative thereof or a solvate of any of the foregoing.

The compounds of formula (I) and their physiologically functional derivatives are hereinafter referred to as compounds according to the invention.

In another aspect of the present invention there are provided the compounds according to the invention for use in therapy more particularly for use as an antiviral agent, especially for the treatment of hepatitis or retroviral infections of animals, which term is intended to include humans, woodchucks and ducks.

Examples of retroviral infections which may be treated or prevented in accordance with the invention include human retroviral infections such as Human Immunodeficiency Virus (HIV), for example, HIV-1 or HIV-2, and Human T-cell Lymphotropic Virus (HLTV), for example, HTLV-I or HTLV-II, infections. The compounds according to the invention are especially useful for the treatment of AIDS and related clinical conditions such as AIDS-related complex (ARC), progressive generalized lymphadenopathy (PGL), Kaposi's sarcoma, thrombocytopenic purpura, AIDS-related neurological conditions, such as multiple sclerosis or tropical paraperesis, and also anti-HIV antibody-positive and HIV-positive conditions, including such conditions in asymptomatic patients.

The compounds according to the invention may also be used in the treatment of psoriasis.

An example of a hepatitis infection which may be treated or prevented in accordance with the invention is an hepatitis B virus infection.

In a further aspect of the present invention there is included:

a) A method for the treatment or prevention of the symptoms or effects of a viral infection, particularly a hepatitis or retroviral infection in an infected animal, for example, a mammal, such as a human, which comprises treating said animal with a therapeutically effective amount of a compound according to the invention. According to a particular embodiment of this aspect of the invention, the viral infection is an HBV or HIV infection.

b) A method for the prophylaxis of a viral infection, particularly an HBV or HIV infection in an animal, for example, a mammal including a human, which comprises treating said animal with a therapeutically effective amount of a compound according to the invention.

c) A method of treatment of an animal subject suffering from or liable to suffer from a viral infection, which comprises administering to the said animal an effective amount of a compound according to the invention.

d) Use of a compound according to the invention for the manufacture of a medicament for the treatment or prophylaxis of any of the above-mentioned infections or conditions.

As used herein, the term "physiologically functional derivative" means any physiologically acceptable salt, ester, or salt of such ester, of a compound of formula (I) or a compound which upon administration to the recipient, is capable of providing (directly or indirectly) such a compound or an antivirally active metabolite or residue thereof. For example, it is within the scope of the invention to replace the H of the OH group at the 5'-position is replaceable by a potentially hydrolysable group such as acyl or alkyl.

Preferred esters of the compounds of formula (I) included within the scope of the invention as physiologically functional derivatives include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$ alkyl, or $C_{1-4}$ alkoxy), or amino; sulphonate esters, such as alkyl- or aralkylsulphonyl (for example, methanesulphonyl); amino acid esters (for example, L-valyl or L-isoleucyl); and mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Any reference to any of the above compounds also includes a reference to a physiologically acceptable salt thereof.

Examples of physiologically acceptable salts of the compounds of formula (I) and physiologically acceptable derivatives thereof include salts derived from an appropriate base, such as an alkali metal (for example, sodium), an alkaline earth (for example, magnesium), ammonium and $NX_4^+$ (wherein X is $C_{1-4}$alkyl). Physiologically acceptable salts of an hydrogen atom or an amino group include salts of organic carboxylic acids such as acetic, lactic, tartaric, malic, isethionic, lactobionic and succinic acids; organic sulfonic acids, such as methanesulphonic, ethanesulphonic, benzenesulphonic and p-toluenesulphonic acids, and inorganic acids, such as hydrochloric, sulphuric, phosphoric and sulphamic acids. Physiologically acceptable salts of a compound of an hydroxy group include the anion of said compound in combination with a suitable cation such as $Na^+$, $NH_4^{3O}$ and $NX_4^+$ (wherein X is a $C_{1-4}$ alkyl group).

For therapeutic use, salts of compounds of formula (I) will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

The compounds according to the invention may be employed alone or in combination with other therapeutic agents for the treatment of the above infections or conditions. Combination therapies according to the present invention comprise the administration of at least one compound of the formula (I), (IA), (IB) or (IC) or a physiologically functional derivative thereof and at least one other pharmaceutically active ingredient. The active ingredient(s) and pharmacologically active agents may be administered together or separately and, when administered separately this may occur simultaneously or sequentially in any order. The amounts of the active ingredient(s) and pharmacologically active agent(s) and the relative timings of administration will be selected in order to achieve the desired combined therapeutic effect. Preferably the combination therapy involves the administration of one compound of the formula (I), (IA), (IB) or (IC) or a physiologically functional derivative thereof and one of the agents mentioned herein below.

Examples of such further therapeutic agents include agents that are effective for the treatment of HIV infections or associated conditions such as 3'-azido-3'-deoxythymidine (zidovudine), other 2',3'-dideoxy-nucleosides such as 2',3'-dideoxycytidine, 2',3'-dideoxyadenosine and 2',3'-dideoxyinosine, carbovir, acyclic nucleosides (for example, acyclovir), 2',3'-didehydrothymidine, protease inhibitors such as N-tert-butyl-dechydro-2-[-2(R)-hydroxy-4-phenyl-3 (S)-[[N-(2-quinolylcarbonyl)-L-asparginyl]butyl]-(4aS,8aS) -isoquinoline-3(S)-carboxamide (Ro 31-8959), oxathiolan nucleoside analogues such as cis-1-(2-hydroxymethyl)-1,3-oxathiolan-5-yl)-cytosine or cis-1-(2-(hydroxymethyl)-1,3-oxathiolan-5-yl)-5-fluoro-cytosine, 3'-deoxy-3'-fluoro-thymidine, 2',3'-dideoxy-5-ethynyl-3'-fluorouridine, 5-chloro-2'3'-dideoxy-3'fluorouridine, Ribavirin, 9-[4-hydroxy-2-(hydroxymethyl)but-1-yl]guanine(H2G), TAT inhibitors such as 7-chloro-5-(2-pyrryl)-3H-1,4-benzodiazepin-2(H)-one (Ro5-3335), or 7-chloro-1,3-dihydro-5-(1H-pyrrol-2-yl)-3H-1,4-benzodiazepin-2-amine (Ro24-7429) interferons such as α-interferon, renal excretion inhibitors such as probenecid, nucleoside transport inhibitors such as dipyridamole; pentoxifylline, NAcetylCysteine, Procysteine, α-trichosanthin, phosphonoformic acid, as well as immunodulators such as interleukin II, granulocyte macrophage colony stimulating factors, erythropoetin, soluble $CD_4$ and genetically engineered derivatives thereof. Examples of such further therapeutic agents which are effective for the treatment of HBV infections include carbovir, oxathiolan nucleoside analogues such as cis-1-(2-hydroxymethyl)-1,3-oxathiolan-5-yl)-cytosine or cis-1-(2-(hydroxymethyl)-1,3-oxathiolan-5-yl-5-fluoro-cytosine, 2',3'-dideoxy-5-ethynyl-3'-fluorouridine, 5-chloro-2',3'-dideoxy-3'-fluorouridine, 1-(β-D-arabinofuranosyl)-5-propynyluracil, acyclovir and interferons, such as α interferon.

More preferably the combination therapy involves the administration of one of the above-mentioned agents together with one of the compounds of formula (I), (IA), (IB) or (IC) specifically named herein.

The present invention further provides pharmaceutical formulations of the compounds according to the invention, also referred to herein as active ingredients, which may be administered for therapy to a mammal including a human ("the recipient") by any suitable route appropriate to the clinical condition to be treated; suitable routes include oral, rectal, nasal, topical (including buccal, sublingual and transdermal), vaginal and parenteral (including subcutaneous, intramuscular, intravenous and intradermal). It will be appreciated that the preferred route will vary with the condition, weight, age and sex of the recipient, the nature of the infection and the chosen active ingredient.

The amount of a compound of the invention required for the treatment of the above named viral infections, including HBV and HIV infections will depend on a number of factors including the severity of the condition to be treated and the identity of the recipient and will ultimately be at the discretion of the attendant physician.

In general, a suitable dose for the treatment of a viral infection, such as in HBV or HIV infection, is in the range 0.5 to 120 mg per kilogram body weight of the recipient per day, preferably in the range 1 to 90 mg per kilogram body weight per day and most preferably in the range 2 to 60 mg per kilogram body weight per day. An optimum dose is about 10 mg per kilogram body weight per day. Unless otherwise indicated all weights of active ingredients are calculated as the parent compounds of formula (I). In the case of a physioiogically acceptable salt, ester or other physiologically functional derivative of a compound of formula (I) or a solvate of any thereof the figures would be increased proportionately. The desired dose is preferably presented as two, three, four, five, six, or more sub-doses administered at appropriate intervals throughout the day. These sub-doses may be administered in unit dosage forms, for example, containing from 1 to 1500 mg, preferably from 5 to 1000 mg, most preferably from 10 to 700 mg of active ingredient per unit dosage form. Alternatively, if the condition of the recipient so requires, the dose may be administered as a continuous infusion.

Ideally, the active ingredient should be administered to achieve peak plasma concentrations of the active compound of from about 0.25 to about 100 µM, preferably from about 0.5 to 70 µM, most preferably from about 1 to about 50 µM. This may be achieved, for example, by the intravenous injection of a 0.1 to 5% w/v solution of the active ingredient, optionally in saline, or orally administered, for example, as a tablet, capsule, or syrup containing from about 0.5 to about 100 mg/kg of the active ingredient. Desirable blood levels may be maintained by a continuous infusion to provide from about 0.01 to about 5.0 mg/kg/hour or by intermittent infusions containing from about 0.4 to about 15 mg/kg of the active ingredient.

While it is possible for the active ingredient to be administered alone, it is preferable to present it as a pharmaceutical formulation. The formulations of the present invention comprise at least one active ingredient, as defined above, together with one or more acceptable carriers thereof and, optionally, one or more other therapeutic agents. Each carrier must be "acceptable" in the sense of being compatible with the other ingredients of the formulation and not injurious to the patient.

Formulations of the invention include those suitable for administration by any of the aforementioned routes which may conveniently be presented in unit dosage form and may be prepared by any method well know in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers, or both, and then, if necessary, shaping the product.

Formulations of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary, or paste or may be contained within liposomes.

A tablet may be made by compression or moulding, optionally with one or more accessory ingredients. Compressed tablets may be prepared by compressing in a suitable machine the active ingredient in a free-flowing form such as a powder or granules, optionally mixed with a binder (for example, povidone, gelatin, hydroxypropylmethyl cellulose), lubricant, inert diluent, preservative, disintegrant (for example, sodium search glycollate, cross-linked povidone, crossed-linked sodium carboxmethyl cellulose), or a surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile or to be soluble or effervescent when added to liquid. Tablets may optionally be provided with an enteric coating, to provide release in parts of the gut other than the stomach.

Formulations suitable for oral use may also include buffering agents designed to neutralise stomach acidity. Such buffers maybe chosen from a variety of organic or inorganic agents such as weak acids or bases admixed with their conjugated salts.

A capsule may be made by filling a loose or compressed powder on an appropriate filling machine, optionally with one or more additives. Examples of suitable additives include binders such as povidone; gelatin, lubricants, inert diluents and disintegrants as for tablets. Capsules may also be formulated to contain pellets or discrete sub-units to provide slow or controlled release of the active ingredient. This can be achieved by extruding and spheronising a wet mixture of the drug plus an extrusion aid (for example microcrystalline cellulose) plus a diluent such as lactose. The spheroids thus produced can be coated with a semipermeable membrane (for example ethyl cellulose, Eudragit WE30D) to produce sustained release properties.

An edible foam or whip formulation ideally comprises; 50–70% of an edible oil, particularly a vegetable oil, including corn oil, peanut oil, sunflower oil, olive oil and soybean oil; 2–10% of one or more surfactants particularly lecithin, polyols, polyol polymer esters including glyceryl fatty acid esters, polyglyceryl fatty acid esters (e.g. decaglycerol tetraoleate), or sorbitan fatty acid esters (e.g. sorbitan monostearate); 1–4% of a propellant which is suitable for ingestion, notably a compressed gas propellant especially nitrogen, nitrous oxide or carbon dioxide, or a gaseous hydrocarbon especially propane, butane or isobutane; 0.5–30% of one or more viscosity modifiers of particle size in the range 10–50 microns in diameter, particularly powdered sugars or colloidal silicon dioxide; and optionally 0.5–1% of one or more suitable, non-toxic colourings, flavourings or sweetners. The active ingredient is preferably present in such formulations in a concentration of 10–46%, advantageously 30%. An edible foam or whip formulation as described above may be prepared in a conventional manner, for example by mixing the edible oil, surfactant(s) and any other soluble ingredients, adding the viscosity modifier(s) and milling the mixture to form a uniform dispersion and suspension. The active ingredient is blended into the milled mixture until evenly dispersed. Finally, a metered quantity of propellant is incorporated to the mixture after said mixture has been measured into a suitable dispensing container.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved in an adhesive or 3) dispersed in a polymer. A suitable concentration of the active compound is about 1% to 35%, preferably about 3% to 15%. As one particular possibility, the active compound may be delivered from the patch by iontophoresis as generally described in Pharmaceutical Research, 3(6), 318 (1986).

Pharmaceutical formulations for topical administration according to the present invention may be formulated as an ointment, cream, suspension, lotion, powder, solution, paste, gel, spray, aerosol or oil. Alternatively, a formulation may comprise a dressing such as a bandage or adhesive plaster impregnated with active ingredients and optionally one or more excipients or diluents.

For infections of the eye or other external tissues, for example mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base or as a water-in-oil base.

If desired, the aqueous phase of the cream base may include, for example, at least 40–45% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may include a compound which enhances absorption or penetration of the active ingredient through the skin or other affected areas. Examples of such dermal penetration enhancers include dimethylsulphoxide and related analogues.

The oily phase of an emulsion formulation according to the invention may comprise merely an emulsifier (otherwise known as an emulgent), but desirably comprises a mixture of at least one emulsifier with a fat or an oil or with both a fat and an oil. Preferably, a hydrophilic emulsifier is included together with a lipophilic emulsifier which acts as a stablilizer. It is also preferred to include both an oil and a fat. Together, the emulsifer(s) with or without stabilizer(s) make up the so-called emulsifying wax, and the wax together with the oil and/or fat make up the so-called emulsifying ointment base which forms the oily phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These maybe used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent. The ingredient is preferably present in such formulations in a concentration of 0.5 to 20%, advantageously 0.5 to 10%, particularly about 1.5% w/w.

Formulations suitable for topical administration in the mouth include lozenges comprising the active ingredient in a flavoured material, usually sucrose and acacia or tragacanth; pastilles comprising the active ingredient in an inert material such as gelatin and glycerin, or sucrose and acacia; and mouth-washes comprising the active ingredient in a suitable liquid carrier.

Formulations for rectal administration may be presented as a suppository with a suitable base comprising for example cocoa butter or higher fatty alcohol (e.g. hard wax, European Pharmacopoeia) or triglycerides and saturated fatty acids (e.g. Witepsol).

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or sub-dose, as herein above recited, or an appropriate fraction thereof, of an active ingredient.

It should be understood that in addition to the ingredients particularly mentioned above, the formulations of this invention may include other agents conventional in the art having regard to the type of formulation in question, for example those suitable for oral administration may include flavouring agents.

The compounds according to the invention may also be presented for the use in the form of veterinary formulations, which may be prepared, for example, by methods which are conventional in the art.

The present invention further includes a process for the preparation of a compound of formula (I), (IA), (IB), (IC) and salts, esters or physiologically functional derivatives thereof or a solvate of any of the foregoing, which comprises either:

(A) reacting a purine base of formula (II)

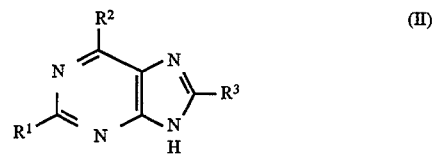

wherein $R^1$, $R^2$ and $R^3$ are as hereinbefore defined, or a functionally equivalent thereof with a compound of formula (III)

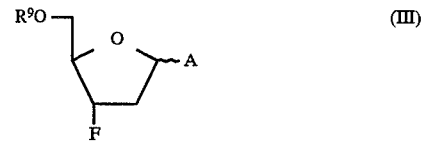

wherein $R^9$ represents hydrogen or a hydroxy protecting group and A is a phosphate group or salt thereof or a purine or pyrimidine moiety other than (II) or a leaving group, to form a compound of formula (I); or (B) reacting a compound of formula (IV)

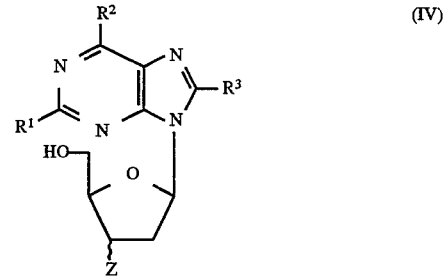

wherein $R^1$, $R^2$ and $R^3$ are as hereinbefore defined and Z represents a precursor group for the fluoro atom, with agent(s) and/or under conditions serving to convert the precursor group Z to a fluoro atom in the erythro configuration;

and thereafter, or simultaneously therewith, effecting one or more of the following optional conversions:
(i) removing any remaining protecting group(s);
(ii) when a compound of formula (I), (IA), (IB) or (IC) is formed, converting it into a salt, ester or physiologically functional derivative thereof; or
(iii) when a salt, ester or physiologically functional derivative of a compound of formula (I), (IA), (IB) or (IC) is formed or a solvate of any thereof, converting the derivative into a compound of formula (I), (IA), (IB) or (IC) or into a different derivative of the compound of formula (I), (IA), (IB) or (IC).

In the above-described process according to the invention the starting compounds of formulae (II), (III) and (IV), as well as the above-mentioned agents and conditions, may be selected from those which are known in the art of nucleoside synthetic chemistry. Examples of such conversion procedures are described hereinafter for guidance and it will be understood that they may be modified in conventional manner depending on the desired compound of formula (I). In particular, where a conversion is described which would otherwise result in the undesired reaction of labile groups, then such groups may be protected in conventional manner with subsequent removal of the protecting group(s) after completion of the conversion.

According to the conditions employed to effect process A, the purine base of formula (II) and the compound of formula (III) may or may not be protected using conventional protecting groups, such as acyl groups, for example, alkanoyl (for example, acetyl), substituted alkanoyl, such as alkoxyalkanoyl, aroyl (for example, benzoyl), ether groups, for example, trialkylsilyl groups, such as t-butyldimethylsilyl or other groups, such as aralkyl (for example, benzyl) or a phosphate group.

Such groups maybe removed by acid or base hydrolysis, hydrogenolysis, or enzymatically. Acyl groups are typically removed by base hydrolysis and silyl groups by acid hydrolysis or fluoride ion. Aralkyl groups such as benzyl are advantageously removed by catalytic hydrogenolysis.

Two methods are commonly employed to effect process A, viz enzymatic and chemical.

Process (A) may be effected enzymatically by, for example, reacting an appropriate purine base of formula (II), wherein $R^1$, $R^2$ and $R^3$ are as hereinbefore defined or a functional equivalent of any thereof, for example, a salt or protected derivative thereof (see above); with a compound of formula (III) wherein $R^9$ is hydrogen or a hydroxy protecting group (see above) and A is a purine or pyrimidine moiety (other than (II)), a phosphate group or a salt thereof.

In the case where A is a purine or pyrimidine moiety (other than (II)), the reaction may be carried out in the presence of (i) phosphorylase enzymes, such as purine nucleoside phosphorylase and thymidine phosphorylase and an in organic phosphate or salt thereof; or (ii) a transferase enzyme, for example, N-deoxyribosyl transferase.

In order to obtain the compounds of the invention it is necessary when employing this method that the compound of formula (III) should be in its β-form.

The N-deoxyribosyl transferase may be isolated by standard biochemical techniques from:

(i) *E. coli* strain SS6030/14, which expresses lactobacillus enzyme, available from the American Type Culture Collection (ATCC) Rockville, Md., from 18th Jul., 1990 under Accession No. ATCC 68367, or (ii) *E. coli* strain SS70-8/15 which expresses lactobacillus enzyme, available from the ATCC from 17th Jun., 1992 under Accession No. ATCC 69016.

In the case where A represents a phosphate group or a salt thereof, the reaction may be carried out in the presence of a single phosphorylase enzyme, such as purine nucleoside phosphorylase. In order to obtain the compounds of the invention it is necessary when employing this method that the compound of formula (III) should be in its α-form.

Protecting groups may be used in the enzymatic process but in practice have been found to be unnecessary and in some cases to be actually disadvantageous in terms of overall yield.

Process (A) may be effected chemically by, for example, reacting a compound of formula (II) as hereinbefore defined with a compound of formula (III) wherein $R^9$ is hydrogen or a hydroxy protecting group and A represents a suitable leaving group, such as a halogen atom, for example, chlorine, an acyloxy group, such as acetoxy or an alkoxy group, for example, methoxy, in the presence of a catalyst, such as tin (IV) chloride or trimethylsilyltriflate, in a suitable solvent, such as acetonitrile.

In contrast to the enzymatic method it has been found that in the chemical process (a) the compounds of formula (II) and (III) may advantageously be protected (vide supra) and (b) the compound of formula (I) so formed is a mixture of α- and β-anomers. The β-anomers of the present invention may be obtained by anomeric separation by methods well known to a skilled person or readily available in the chemical literature, for example, by silica gel column chromatography or HPLC.

Compounds of formula (II) wherein $R^1$, $R^2$ and $R^3$ are as hereinbefore defined or a functional equivalent of any thereof may be obtained commercially, for example, from the Aldrich Chemical Company or prepared by conventional methods well known to a skilled person or readily available from the chemical literature, for example, by methods the same as or analogous to those described in Robins et al., J. Amer. Chem. Soc., 1957, 79, 490–494 and Montgomery and Temple, J. Amer. Chem. Soc., 1961, 83, 630–635.

For example, purine bases wherein $R^1$ is amino or hydrogen $R^3$ is hydrogen and $R^2$ is, for example, methylmercapto or benzylamino may be obtained commercially from the Aldrich Chemical Co.

Purine bases of formula (II) wherein $R^1$ is amino or hydrogen, $R^2$ is as hereinbefore defined and $R^3$ is hydrogen may be conveniently prepared from commercially available 2-amino-6-chloropurine or 6-chloropurine (Sigma Chemical Co.). 2-Amino-6-O-substituted purines may be prepared from 2-amino-6-chloropurine by treatment with sodium and the appropriate alcohol. For example, 2-amino-6-benzyloxypurine may be prepared by the reaction of 2-amino-6-chloro purine with benzyl alcohol. 2-Amino-6-N-substituted purines may be prepared by treatment of 2-amino-6-chloropurine with the appropriate amine or a compound of formula (VI):

(VI)

(wherein n is an integer of from 3 to 6) in the presence of an organic solvent, such as acetonitrile, or an alcohol, such as methanol.

2-Amino-6-S-substituted purines may conveniently be prepared by treatment of 2-amino-6-mercapto purine with the appropriate moiety having a suitable leaving group. For example, compounds of formula (II) wherein $R^1$ represents —$S(O)_nR^6$ wherein $R^6$ is $C_{6-10}$ aryl, such as phenyl, may advantageously be prepared by treatment of the 2-amino-6-mercapto-purine with chlorophenyl in an organic solvent, such as acetonitrile, in the presence of an organic base such as triethylamine, under nitrogen. 2-Amino-6-mercapto purine may be obtained commercially from the Aldrich Chemical Co.

Compounds of formula (III) wherein A is a pyrimidine or purine moiety may conveniently be prepared by methods well known to a skilled person or readily available from the chemical literature. For example, 2',3'-dideoxy-3'-fluorouridine may be obtained commercially or prepared by the method described by G. Kowollick et al., J. Prakt. Chem., 1973, 315(5), 895. 3'-deoxy-3'-fluorothymidine may be prepared by the method described by Etzold et al., Tetrahedron, 1971, 27, 2463–2472 and 2',3'-dideoxy-3'-fluoroguanine may be prepared by the method of Herdewijn et al., J. Med. Chem., 1988, 31, 2040–2048.

Compounds of formula (III) wherein A represents a phosphate group may be prepared chemically by methods analogous to those available in the chemical literature or from compounds of formula (III) wherein A is a pyrimidine or purine moiety by treatment with a phosphorylase enzyme, such as thymidine phosphorylase.

Compounds of formula (III) wherein $R^9$ is as hereinbefore defined and A represents a leaving group, such as methoxy, may be obtained commercially or maybe prepared according to the method of Asahi Glass as described in Japanese Patent Application No. JP0129390.

With regard to process (B), this may be effected, for example, by treatment of a compound of formula (IV) in which Z represents a leaving group, for example, hydroxy or an organosulphonyloxy, such as methanesulphonyloxy or trifluoromethanesulphonyloxy, with an appropriate fluorinating agent, such as diethylaminosulphurtrifluoride, potassium fluoride, potassium hydrogen fluoride, or tetra-butyl-ammonium fluoride.

Compounds of formula (IV) may be prepared by methods well known to a skilled man or readily available from the chemical literature, for example, by the method of Herdewijn et al., J. Med-Chem., 1988, 31, 2040–2048.

Esters according to the invention may be prepared by methods known in the art. For example, by treatment of the parent compound of formula (I) with an appropriate esterifying agent, for example, by treatment with an appropriate acid halide, for example, chloride or anhydride.

A compound of formula (I), (IA), (IB) or (IC) may be converted into a corresponding physiologically acceptable ether of formula (I), (IA), (IB) or (IC) by reaction with an appropriate alkylating agent in a conventional manner.

The compounds of formula (I), (IA), (IB) or (IC) including esters thereof, may be converted into physiologically acceptable salts in a conventional manner, for example, by treatment with an appropriate base. An ester or salt of a compound of formula (I), (IA), (IB) or (IC) may be converted into the parent compound by, for example, hydrolysis.

According to a further aspect of the invention, there are also provided:

(a) a compound of formula (IA) or (IB) or (IC) or a salt, ester or physiologically functional derivative of any thereof or a solvate of any of the foregoing;

(b) a compound of formula (IA) or (IB) or (IC) or a salt, ester or physiologically functional derivative of any thereof or a solvate of any of the foregoing for use in therapy, more particularly for use as an antiviral agent, especially for the treatment of an hepatitis (eg. HBV) or retrovirus (eg. HIV) infection of animals, which terms is intended to include humans, woodchucks and ducks.

(c) the use of a compound of formula (IA) or (IB) or (IC) or a salt, ester or physiologically functional derivative of any thereof or a solvate of any of the foregoing for the manufacture of a medicament for the treatment or prophylaxis of a hepatitis virus infection, for example, HBV or a retroviral infection, particularly an HIV infection.

(d) a method for the treatment or prevention of the symptoms or effects of a viral infection, particularly a hepatitis or retroviral infection in an infected animal, for example, a mammal such as a human, which comprises treating said animal with a therapeutically effective amount of a compound of formula (IA) or (IB) or (IC) or a salt, ester of physiologically functional derivative of any thereof or a solvate of any of the foregoing.

(e) a pharmaceutical formulation comprising a compound of formula (IA) or (IB) or (IC) or a salt, ester or physiologically functional derivative of any thereof or a solvate of any of the foregoing, together with a pharmaceutically acceptable carrier therefor.

The following Examples are intended for illustration only and are not intended to limit the scope of the invention in any way. The term "active ingredient" as used in the Examples means a compound of formula (I), (IA), (IB), (IC) or a salt, ester or physiologically functional derivative thereof or a solvate of any thereof.

SYNTHETIC EXAMPLES

A. Preparation of trans-N-deoxyribosylase (E.C. 2.4.2.6) from *Esherichia coli*

*E. coli* strain SS6030/14 or SS70-8/15 was grown overnight (15–20 hr) in a rich medium, such as Luria broth, containing 150 g/mL ampicillin. The bacteria were collected from the growth medium by centrifugation at 4° C. and the cell pellet washed with cold, 100 mM sodium phosphate buffer, pH 6.0. A cell extract was prepared by resuspending the washed cell pellet with 0.6–0.8 volumes of cold, 100 mM sodium phosphate buffer followed by passage of the cell suspension through a French press at 12–14 Kpsi. Whole cells and cell debris were removed by centrifugation in a 70Ti rotor and 50 Krpm for 90 min. The supernatant obtained following centrifugation was the high speed supernatant (HSS). The $A_{260}$ for the HSS was adjusted to equal 180 by addition of cold, 100 mM sodium phosphate buffer. The diluted HSS was adjusted to 0.2% PEI (polyethyleneimine), incubated at 4° C. for 15–30 min and then centrifuged. The supernatant obtained following the PEI precipitation was adjusted no 30% saturation with respect to $(NH_4)_2SO_4$, incubated at 4° C. for 60–90 min and then centrifuged to pellet the protein. The protein precipitated with 30% $(NH_4)_2SO_4$ was slowly dissolved in 100 mM sodium phosphate buffer (pH 6.0) and then dialyzed against 2 to 6 liters of the same buffer.

After dialysis, the precipitate that formed was removed by centrifugation. The supernatant containing enzyme was heated 5–10 min in a 60° C. water bath followed by a 20 min incubation in a ice/water slurry. The precipitate that formed during the heat treatment step was removed by centrifugation. The supernatant contained trans-N-deoxyribosylase which was used for nucleoside synthesis.

The trans-N-deoxyribosylase activity of each enzyme preparation was quantitated using deoxyinosine and cytosine as substrates in the xanthine oxidase coupled assay system described by Cardinaud, R. 1978. Nucleoside Deoxyribosyltransferase from *Lactobacillus helveticus*. Methods Enzymol. 51:446–455.

*E. coli* strain SS6030/14 was deposited at the American Type Culture Collection (ATCC) Rockville, Md. 20852-1776 on 18th Jul., 1990 under Accession No. ATCC 68367 and *E. coli* strain SS70-8/15 was deposited at the ATCC Rockville, Md. 20852-1776 on 17th Jun., 1992, under Accession No. ATCC 69016.

EXAMPLE 1

6-Cyclopropylmethylamino-9-(2,3-dideoxy-3-fluoro-β-D-erythro-pentofuranosyl)-9H-purine 6-Cyclopropylmethylamino-9H-purine was prepared by nucleophilic displacement of the chlorine group on 6-chloropurine (Aldrich Chemical Company) by cyclopropylmethylamine (Karl Industries), in methanol.

6-Cyclopropylmethylamino-9H-purine (1.0 g 5.8 mmoles) and 2',3'-dideoxy-3'-fluorouridine (obtained commercially or by the method described by G. Kowollick et al., J. Prakt. Chem., 1973 315(5), pp895) (1.13 g 4.9 mmoles) were suspended in potassium phosphate buffer (10 mM, 100 ml), pH 6.8, containing 0.04% potassium azide. Purified purine nucleoside phosphorylase (1070 I.U.) and thymidine phosphorylase (400 I.U.) (Krenitsky, et al, *Biochemistry*, 20, 3615 (1981) and U.S. Pat. No. 4,381,344) were added to the reaction mixture and the suspension stirred at 37° C. After 14 days, potassium phosphate buffer (10 mM, 25 ml), pH 6.8, containing 0.04% potassium azide was added. Additional purine nucleoside phosphorylase (5400 I.U.) and thymidine phosphorylase (2000 I.U.) were added after 17 days. After a total reaction time of 33 days, the reaction was filtered and the filtrate applied to a series of coupled columns. The initial column contained AG1-X2 (2.5×10 cm, OH⁻ form), while the second column contained Amberlite XAD-2 resin (2.5×20 cm). After sample application, the columns were washed with $H_2O$ (800 ml) and eluted with MeOH. Product containing fractions were then flash chromatographed on silica gel (2.5×20 cm) using $CH_2Cl_2$:MeOH (9:1). Solvent was removed and lyophilization yielded 6-cyclopropylmethyl-amino-9(2,3-dideoxy-3-fluoro-β-D-erythro-pentofuranosyl)-9H-purine (0.60 g).

Elemental analysis for $C_{14}H_{18}FN_5O_2$ Calculated: C,54.72; H,5.90; F,6.18; N,22.79 Found: C,54.80; H,6.02; F,5.94; N,22.58

¹H NMR and mass spectral data were consistent with the structure.

EXAMPLE 2

2-Amino-9-(2,3-dideoxy-3-fluoro-β-D-erythro-pentofuranosyl)-6-methylmercapto-9H-purine 2-Amino-6-methylmercapto-9H-purine (0.49 g 2.7 mmoles, Aldrich Chemical Company), and 2',3'-dideoxy-3'-fluorouridine (0.50 g 2.2 mmoles) were suspended in potassium phosphate buffer 50 ml (10 mM), pH 6.8, containing 0.04% potassium azide. Purified purine nucleoside phosphorylase (7850 I.U.) and thymidine phosphorylase (2000 I.U.) (Krenitsky et al., *Biochemistry*, 20, 3615 (1981) and U.S. Pat. No. 4,381,344) were added to the reaction mixture and the suspension stirred at 45° C. After 17 days, additional purine nucleoside phosphorylase (7850 I.U.) and thymidine phosphorylase (2000 I.U.) were added. After another 104 days, additional purine nucleoside phosphorylase (15,700 I.U.) and thymidine phosphorylase (52,500 I.U.) were added. Four days later the reaction was poured into methanol 600 ml and denatured protein was removed by filtration through Celite. The filtrate was applied to an AG1-X2 column (2.5×10 cm, OH⁻ form) and the product was eluted with methanol. Solvent was removed in vacuo and the residue flash chromatographed on silica gel (2.5×20 cm) using dichloromethane:methanol (95:5). Solvent was removed and lyophilization yielded 2-amino-9-(2,3-dideoxy-3-fluoro-β-D-erythro-pentofuranosyl)-6-methylmercapto-9H-purine (0.31 g).

Elemental analysis for $C_{11}H_{14}FN_5O_2S$ Calculated: H,44.14; H,4.71; F, 6.35; N,23.40; S,10.71 Found: C,44.41; H,4.67; F,6.16; N,23.21; S,10.57

¹H NMR and mass spectral data were consistent with the structure.

EXAMPLE 3

6-Benzylmercapto-9-(2,3-dideoxy-3-fluoro-β-D-erythro-pentofuranosyl)-9H-purine

6-Benzylmercapto-9H-purine (0.49 g, 2.0 mmoles, Sigma Chemical Company) and 2',3'-dideoxy-3'-fluorouridine (0.32 g, 1.4 mmoles) were suspended in potassium phosphate buffer (10 mM) 100 ml), pH 6.8, containing 0.04% potassium azide. Purified purine nucleoside phosphorylase (1070 I.U.) and thymidine phosphorylase (400 I.U.) (Krenitsky et al., *Biochemistry*, 20, 3615 (1981) and U.S. Pat. No. 4,381,344) were added to the reaction mixture and the suspension stirred at 45° C. After 3 days, additional purine nucleoside phosphorylase (10,700 I.U.) and thymidine phosphorylase (4000 I.U.) were added. Four days later, methanol was added to the reaction mixture to precipitate protein. The protein was removed by filtration and the filtrate applied to a series of coupled columns. The first column contained AG1 resin (2.5×10 cm, OH⁻ form) and the second column contained XAD resin (2.5×20 cm). The columns were washed with water 300 ml and the product removed with methanol. Product fractions were pooled and solvent was removed in vacuo. The residue was flash chromatographed on silica gel (2.5×20 cm) using chloroform:methanol (199:1). Solvent was removed and lyophilization yielded 6-benzylmercapto-9-(2,3-dideoxy-3-fluoro-β-D-erythro-pentofuranosyl)-9H-purine (0.41 g).

Elemental analysis for $C_{17}H_{17}FN_4O_2S \cdot 0.15H_2O \cdot 0.1C_2H_6O$ Calculated: C,56.18; H,4.91; F,5.17; N,15.24 Found: C,56.50; H,4.58; F,4.95; N,14.92

¹H NMR and mass spectral data were consistent with the structure.

EXAMPLE 4

2-Amino-6-diethylamino-9-(2,3-dideoxy-3-fluoro-β-D-erythro-pentofuranosyl)-9H -purine 2-Amino-6-diethylamino-9H-purine was prepared by nucleophilic displacement of the chlorine group on 2-amino-6-chloropurine (Aldrich Chemical Company), by diethylamine (Aldrich Chemical Company), in methanol.

2-Amino-6-diethylamino-9H-purine (0.47 g 2.3 mmoles) and 2',3'-dideoxy-3'-fluorouridine (0.41 g, 1.8 mmoles) were suspended in potassium phosphate buffer (10 mM) 50 ml), pH 6.8, containing 0.04% potassium azide. Purified purine nucleoside phosphorylase (5350 units) and thymidine phosphorylase (2000 unit (Krenitsky et al., *Biochemistry*, 20, 3615 (1981) and U.S. Pat. No. 4,381,344) were added to the reaction mixture and the suspension stirred at 45° C. After 14 days, additional purine nucleoside phosphorylase (15,700 units) and thymidine phosphorylase (4000 units) were added to the reaction mixture. After a total reaction time of 123 days, denatured protein was removed by filtration and the filtrate was applied to a column of AG1-X2 (2.5×10 cm, OH⁻ form). After the column was washed with methanol, fractions containing product were pooled, evaporated and chromatographed on silica gel (2.5×20 cm) using dichloromethane:methanol (97:3). Solvent was removed and lyophilization yielded 2-amino-6-diethylamino-9-(2,3-dideoxy-3-fluoro-β-D-erythro-pentofuranosyl)-9H-purine.

Elemental analysis for $C_{14}H_{21}FN_6O_2 \cdot 0.15H_2O$ Calculated: C,51.41; H,6.56; F,5.81; N,25.70 Found: C,51.67; H,6.39; F,5.43; N,25.52

¹H NMR and mass spectral data were consistent with the structure.

EXAMPLE 5

2-Amino-6-cyclopropylmethylamino-9-(2,3-dideoxy-3-fluoro-β-D-erythro-pentofuranosyl)-9H-purine 2-Amino-6-N-cyclopropylmethylaminopurine was prepared by nucleophilic displacement of the chlorine group on 2-amino-6-chloropurine by cyclopropylmethylamine (Sigma Chemicals), in methanol.

2-Amino-6-N-cyclopropylmethylamino-9H-purine (2.73 g 11.8 mmoles) and 2',3'-dideoxy-3'-fluorouridine (1.81 g 7.9 mmoles) were suspended in potassium phosphate buffer (10 mM) 100 ml), pH 6.8, containing 0.04% potassium azide. Purified purine nucleoside phosphorylase (5350 I.U.) and thymidine phosphorylase (2000 I.U.) (Krenitsky et al., Biochemistry, 20, 3615 (1981) and U.S. Pat. No. 4,381,344) were added to the reaction mixture and the suspension stirred at 45° C. After 14 days, additional purine nucleoside phosphorylase (15,700 units) and thymidine phosphorylase (4000 units) was added. After an additional 39 days, the reaction mixture was filtered to remove denatured protein. The filtrate was applied to a series of coupled columns. The first column contained AG-1 (2.5×10 cm, OH⁻ form) and the second column contained XAD-2 (2.5×20 cm). The columns were flushed with water 500 ml before elution with MeOH. Solvent was removed in vacuo and the residue flash chromatographed on silica gel (2.5×20 cm) using dichloromethane:methanol (95:5). Product containing fractions were pooled and rechromatographed on a second silica gel column (2.4×20 cm) using dichloromethane:acetone (4:1). Solvent was removed and lyophilization yielded 2-amino-6-N-cyclopropyl-methylamino-9-(2,3-dideoxy-3-fluoro-β-D-erythro-pentofuranosyl)-9H-purine (0.37 g).

Elemental analysis for $C_{14}H_{19}FN_6O_2 \cdot 0.60H_2O$ Calculated: C,50.47; H,6.11; F,5.70; N,25.23 Found: C,50.76; H,5.86; F,5.83; N,24.89

$^1$H NMR and mass spectral data were consistent with the structure.

EXAMPLE 6

6-Benzylamino-9-(2,3-dideoxy-3-fluoro-β-D-erythro-pentofuranosyl)-9H-purine

6-Benzylamino-9H-purine (0.46 g 2.1 mmoles, Sigma Chemical Company) and 2',3'-dideoxy-3'-fluorouridine (0.31 g 1.4 mmoles) were suspended in potassium phosphate buffer (10 mM) 100 ml), pH 6.8, containing 0.04% potassium azide. Purified purine nucleoside phosphorylase (2700 I.U.) and thymidine phosphorylase (1000 I.U.) (Krenitsky et al., Biochemistry, 20, 3615 (1981) and U.S. Pat. No. 4,381, 344) were added to the reaction mixture and the suspension was stirred at 45° C. After 14 days, solvent was removed in vacuo and the residue flash chromatographed on silica gel (2.5×20 cm) using dichloromethane:methanol (97:3). Solvent was removed and lyophilization yielded 0.198 g of 6-benzyl-amino-9-(2,3-dideoxy-3-fluoro-β-D-erythro-pentofuranosyl)-9H-purine (0.20 g).

Elemental analysis for $C_{17}H_{18}FN_5O_2 \cdot 0.40H_2O$ Calculated: C,58.24; H,5.41; F,5.42; N,19.98 Found: C,58.47; H,5.26; F,5.19; N,19.92

$^1$H NMR and mass spectral data were consistent with the structure

EXAMPLE 7

2-Amino-6-propylthio-9-(2,3-dideoxy-3-fluoro-β-D-erythro-pentofuranosyl)-9H-purine 2-Amino-6-propylthio-9H-purine was prepared by nucleophilic displacement of the iodo group on 1-iodopropane (Aldrich Chemical Co.) by 2-amino-6-mercapto-9H-purine (Aldrich Chemical Co.) in tetrahydrofuran.

2-Amino-6-propylthio-9H-purine (0.29 g 1.4 mmoles) and 2',3'-dideoxy-3'-fluorouridine (0.39 g, 1.7 mmoles) were suspended in potassium phosphate buffer (10 mM) 90 ml), pH 6.8, containing 0.04% potassium azide. Purified purine nucleoside phosphorylase (370 I.U., PNP) and thymidine phosphorylase (TPase) (Krenitsky et al., Biochemistry, 20, 3615 (1981) and U.S. Pat. No. 4,381,444) adsorbed on to DEAE-cellulose were added to The reaction mixture and the suspension stirred at 45° C. After 2 days, additional PNP (370 I.U.) and TPase adsorbed onto DEAE-cellulose was added. The next day the reaction was filtered to remove the immobilized protein and fresh PNP (2700 I.U.) and TPase (1000 I.U.) was added. After 4 days, additional free PNP (2700 I.U.) and TPase (1000 I.U.) was added to the reaction mixture. After 3 days, PNP (5400 I.U.) and TPase (2000 I.U.) were added. After a total of 14 days, solvent was removed in vacuo and the residue was flash chromatographed on silica gel (2.5×23 cm) using $CH_2Cl_2$:MeOH (97:3). Product-containing fractions were pooled and rechromatographed on a second silica gel column (2.5×20 cm) using $CHCl_3$:MeOH (199:1). Solvent was removed and lyophilization yielded 2-amino-6-propylthio-9-(2,3-dideoxy-3-fluoro-β-D-erythro-pentofuranosyl)-9H-purine (0.14 g).

Elemental analysis for $C_{13}H_{18}FN_5O_2S$ Calculated: C,47.69; H,5.54; F,5.80; N,21.39; S,9.79 Found: C,47.89; H,5.50; F,5.70; N,21.08; S,9.59

$^1$H NMR and mass spectral data were consistent with the structure.

EXAMPLE 8

2-Amino-6-benzyloxy-9-(2,3-dideoxy-3-fluoro-β-D-erythro-pentofuranosyl)-9H-purine 2-Amino-6-benzyloxy-9H-purine was prepared by nucleophilic displacement of the chlorine group on 2-amino-6-chloropurine by the anion of benzyl alcohol (Aldrich Chemical Company). The anion was generated with NaH in tetrahydrofuran.

2-Amino-6-benzyloxy-9H-purine (0.60 g 2.5 mmoles) and 2',3'-dideoxy-3'-fluorouridine (0.5 g 2.2 mmoles) were suspended in potassium phosphate buffer (10 mM) 50 ml, pH 6.8, containing 0.04% potassium azide. Purified purine nucleoside phosphorylase (1070 I.U.) and thymidine phosphorylase (400 I.U.) (Krenitsky et al, Biochemistry, 20, 3615 (1981) and U.S. Pat. No. 4,381,344) were added to the reaction mixture and the suspension stirred at 37° C. After 24 hours, additional thymidine phosphorylase (2000 I.U.) was added and, after 14 days, an additional 10 mM potassium phosphate buffer 25 ml, pH 6.8, containing 0.04% potassium azide was added. Additional purine nucleoside phosphorylase (5400 I.U.) and thymidine phosphorylase (2000 I.U.) were added after 17 days. After a total reaction time of 33 days, denatured protein was removed by filtration. The precipitate was washed with methanol until all the UV absorbing material was eluted from the precipitate. The filtrate was diluted with water until the methanol content was <10% and this diluted sample was applied to a series of coupled columns. The initial column contained AG1-X2 (2.5×10 cm, OH form) while the second column contained XAD-2 (2.5×20 cm). After sample application, the columns were washed with water 800 ml and the product eluted with methanol. Product-containing fractions were flash chromatographed on silica gel (2.5×20 cm) using dichloromethane:methanol (9:1). Solvent was removed and lyophilization yielded 2-amino-6-benzyloxy-9-(2,3-dideoxy-3-fluoro-β-D-erythro-pentofuranosyl)-9H-purine (0.49 g).

Elemental analysis for $C_{17}H_{18}FN_5O_3 \cdot 0.05H_2O$ Calculated: C,56.68; H,5.06; F,5.27; N,19.44 Found: C,56.71; H,5.14; F,5.11; N,19.28

$^1$H NMR and mass spectral data were consistent with the structure.

EXAMPLE 9

9-(2,3-Dideoxy-3-fluoro-β-D-erythro-pentofuranosyl)-6-(hexylamino)-9H-purine

6-Hexylamino-9H-purine (0.67 g, 2.6 mmoles, Sigma Chemical Company) and 2',3'-dideoxy-3'-fluorouridine (0.50 g, 2.2 mmoles) were suspended in potassium phosphate buffer (50 ml, 10 mM), pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615 (1981) and U.S. Pat. No. 4,381,344) immobilized on DEAE cellulose was added to the reaction and the suspension was stirred at 45° C. After 4 days, MeOH (175 ml) was added to the reaction. The reaction was applied to a column containing product were pooled, concentrated, and flash chromatographed on silica gel (2.5×20 cm) with dichloromethane:acetone (92:8). Fractions containing product were pooled, concentrated, and then flash chromatographed again on silica gel (2.5×20 cm) with dichloromethane:acetone (9:1). Solvent was removed and lyophilization yielded 9-(2,3-dideoxy-3-fluoro-β-D-erythro-pentofuranosyl)-6-(hexylamino)-9H-purine (29%) (0.22 g): mp 83° C.;

$[\alpha]_D^{20}$ –17.0 (c=0.5, DMF);

UV $\lambda_{max}$ ($\epsilon \times 10^{-3}$) at pH 7,267 (19.0); at pH 13,267 (18.1);

$^1$H NMR (300 MHz, DMSO-$d_6$) δ8.32 and 8.20 (2s, 2H, $H_2$ and $H_8$), 7.91 (b, 1H, NH), 6.40 (dd, 1H, $H_{1'}$, J=9.4 Hz, J=5.7 Hz), 5.54 (t, 1H, $OH_{5'}$, J=5.8 Hz), 5.44 (dd, 1H, $H_{3'}$, J=53.7 Hz, J=4.4 Hz), 4.25 (dt, 1H, $H_{4'}$, J=27.0 Hz, J=4.4 Hz), 3.60–3.64 (m, 2H, $H_{5'}$ and $H_{5''}$), 3.48 (b, 2H, $NCH_2CH_2(CH_2)_3CH_3$), 2.96–3.10 (m, 1H, $H_{2'}$), 2.58–2.72 (m, 1H, $H_{2''}$), 1.53–1.60 (m, 2H, $NCH_2CH_2(CH_2)_3CH_3$), 1.14–1.33 (m, 6H, $NCH_2CH_2(CH_2)_3CH_3$), and 0.86 (t, 3H, $NCH_2CH_2(CH_2)_3CH_3$, J=6.8 Hz); MS (ci) 338 (M+1), 318 (M-F), 220 ($MH_2$—$C_5H_8FO_2$).

Elemental analysis for $C_{18}H_{24}FN_5O_2$ Calculated: C,56.95; H,7.17; F,5.63; N,20.78 Found: C,56.92; H,7.14; F,5.49; N,20.87

EXAMPLE 10

6-Benzyloxy-9-(2,3-dideoxy-3-fluoro-β-D-erythro-pentofuranosyl)-9H-purine

6-Benzyloxypurine was prepared by nucleophilic displacement of the trimethylamino group on purin-6-yl trimethylammonium chloride (Aldrich Chem. Co.) by benzyl alcohol in the presence of sodium hydroxide.

6-Benzyloxy-9H-purine (0.50 g, 2.3 mmoles) was dissolved in DMF (5 ml) and DMSO (5 ml) 3'-Deoxy-3'-fluorothymidine (0.65 g, 2.7 mmoles) and 10 mM potassium phosphate (40 ml), pH 6.8, containing 0.04% potassium azide were added. Purified purine nucleoside phosphorylase (10,000 I.U.) and thymidine phosphorylase (5,000 I.U.) (Krenitsky et al., *Biochemistry*, 20, 3615 (1981) and U.S. Pat. No. 4,381,344) adsorbed onto 5 ml DEAE-cellulose resin were added to the reaction and the suspension was stirred at 36° C. After 7 days, an additional potassium phosphate (40 ml 10 mM), pH 6.8, containing 0.04% potassium azide were added and the apparent pH readjusted to 6.8. After a total of 16 days of stirring, the reaction was filtered and the filtrate applied to a series of coupled columns. The initial column contained AG1-X2 (OH$^-$ form, 2.5×10 cm) while the second column contained Amberlite XAD-2 resin (2.5×20 cm). After sample application, the columns were washed with a large volume of water and the product was eluted with methanol. Product containing fractions were then flash chromatographed on silica gel (4.8×20 cm) with ethyl acetate. Solvent war removed and lyophilization yielded 6-benzyloxy-9-(2,3-dideoxy-3-fluoro-β-D-erythro-pentofuranosyl)-9H-purine (0.351 g).

Anal. Calculated for $C_{17}H_{17}FN_4O_3$: C,59.30; H,4.98; F,5.52; N,16.27 Found: c,59.34; H,4.90; F,5.88; N,16.11

Mass spectral and NMR data were consistent with the structure.

EXAMPLE 11

2-Amino-9-(2,3-dideoxy-3-fluoro-β-D-erythro-pentofuranosyl)-6-(ethylmethylamino)-9H-purine 2-Amino-6-ethylmethylamino-9H-purine was prepared by displacement of the chlorine group on 2-amino-6-chloropurine (Aldrich Chemical Company) by ethylmethylamine (Aldrich Chemical Company), in methanol.

2-Amino-6-ethylmethylamino-9H-purine (0.5 g, 2.6 mmoles) and 2',3'-dide-oxy-3'-fluorouridine (0.5 g, 2.2 mmoles) were suspended in potassium phosphate buffer (50 ml, 10 mM), pH 7.0, containing potassium azide 0.04%. Purine nucleoside phosphorylase (1120 I.U.) and thymidine phosphory-lase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 7 days, MeOH (170 ml) was added to the reaction. The reaction was applied to a column containing AG1-X2 (OH$^-$ form, 2.5×10 cm) and eluted with MeOH. Fractions containing product were pooled, concentrated, and flash chromatographed on silica gel (2.5×20 cm) with dichloromethane:acetone (92:8). Product containing fractions were again pooled, concentrated, and flash chromatographed on silica gel (2.5×20 cm) with dichloromethane:meth-anol (95:5). Solvent was removed and lyophilization yielded 9-(2,3-dideoxy-3-fluoro-β-D-erythro-pentofura-nosyl)-9H-purine (0.22 g, 32%): mp 89°–9° C.;

$[\alpha]_D^{20}$ –17.2° (c=0.5, DMF);

UV $\lambda_{max}$ ($\epsilon \times 10^{-3}$) at pH 7,284 (15.2); at pH 13,284 (16.7);

$^1$NMR (400 MHz, DMSO-$d_6$) δ7.93 (s, 1H, $H_8$), 6.22 (dd, 1H, $H_{1'}$, J=9.5 Hz, J=5.6 Hz), 5.79 (s, 2H, $NH_2$), 5.44–5.47 (m, 1H, $OH_{5'}$), 5.37 (dd, 1H, $H_{3'}$, J=54.1 Hz, J=4.3 Hz), 4.16 (dt, 1H, $H_{4'}$, J=27.2 Hz, J=4.4 Hz), 3.60 (b, 2H, $CH_3NCH_2CH_3$), 3.55–3.58 (m, 2H, $H_{5'}$ and $H_{5''}$), 3.25 (b, 3H, $CH_3NCH_2CH_3$), 2.76–2.94 (m, 1H, $H_{2'}$), 2.48–2.60 (m, 1H, $H_{2''}$), 1.10 (t, 3H, $CH_3NCH_2CH_3$, J=7.0 Hz);

MS (ci) 311 (M+1), 291 (M-F), 193 ($MH_2$—$C_5H_8FO_2$).

Elemental Analysis for $C_{13}H_{19}FN_6O_2 \cdot 0.25H_2O$ Calculated: C,49.60; H,6.24; F,6.03; N,26.69 Found: C,49.66; H,6.11; F,5.83; N,26.48

EXAMPLE 12

2-Amino-9-(2,3-dideoxy-3-fluoro-β-D-erythro-pentofuranosyl)-6-(methylpropylamino)-9H-purine 2-Amino-6-methylpropylamino-9H-purine was prepared by displacement of the chlorine group on 6-chloropurine (Aldrich Chemical Company) by methylpropylamine (Aldrich Chemical Company), in methanol.

2-Amino-6-methylpropylamino-9H-purine (0.54 g, 2.6 mmoles) and 2',3'-dideoxy-3'-fluorouridine (0.50 g, 2.2 mmoles) were suspended in potassium phosphate buffer, (50 ml, 10 mM), pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 8 days, MeOH (170 ml) was added to the reaction. The reaction was applied to a column containing AG1-X2 (OH⁻ form, 2.5×10 cm) and eluted with MeOH. Fractions containing product were pooled, concentrated, and flash chromatographed on silica gel (2.5×20 cm) with dichloromethane:acetone (92:8). Solvent was removed and lyophilization yielded 2-amino-9-(2,3-dideoxy-3-fluoro-β-D-erythro-pentofuranosyl)-6-(methylpropylamino)-9H-purine (0.40 g, 56%): mp 80°–84° C.;

$[\alpha]_D^{20}$ –17.8° (=0.5, DMF);

UV $\lambda_{max}$ ($\epsilon \times 10^{-3}$) at pH 7,284 (14.9); at pH 13,284 (16.1);

¹H NMR (300 MHz, DMSO-d₆) δ7.93 (s, 1H, H₈), 6.22 (dd, 1H, H₁·, J=9.4 Hz, J=5.6 Hz), 5.79 (s, 2H, NH₂), 5.44–5.47 (m, 1H, OH₅·), 5.38 (dd, 1H, H₃·, J=53.6 Hz, J=4.0 Hz), 4.17 (dt, 1H, H₄·, J=27.5 Hz, J=4.5 Hz), 3.91 (b, 2H, CH₃NCH₂CH₂CH₃), 3.52–3.60 (m, 2H, H₅· and H₅··), 3.25 (b, 3H, CH₃NCH₂CH₂CH₃), 2.72–2.96 (m, 1H, H₂·, 2.46–2.62 (m, 1H, H₂··), 1.52–1.64 (m, 2H, CH₃NCH₂CH₂CH₃), and 0.84 (t, 3H, CH₃NCH₂CH₂CH₃, J=7.3 Hz);

MS (ci) 325 (M+1), 305 (M-F), 207 (MH₂—C₅H₈FO₂).

Elemental Analysis for C₁₄H₂₁FN₆O₂.0.35H₂O Calculated: C,50.85; H,6.61; F,5.75; N,25.42 Found: C,50.95; H,6.40; F,5.51; N,25.30

EXAMPLE 13

2-Amino-9-(2,3-dideoxy-3-fluoro-β-D-erythro-pentofuranosyl)-6-(dimethylamino)-9H-purine 2-Amino-6-dimethylamino-9H-purine was prepared by displacement of the chlorine group on 2-amino-6-chloropurine (Aldrich Chemical Company) by dimethylamine (Aldrich Chemical Company), in methanol.

2-Amino-6-dimethylamino-9H-purine (0.46 g, 2.6 mmoles) and 2',3'-dideoxy-3'-fluorouridine (0.50 g, 2.2 mmoles) were suspended in potassium phosphate buffer (50 ml, 10 mM), pH 7.0, containing potassium azide 0.04%. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 19 days, MeOH (170 ml) was added to the reaction. The reaction was applied to a column containing AG1-X2 (OH⁻ form, 2.5×10 cm) and eluted with MeOH. Fractions containing product were pooled, concentrated, and flash chromatographed on silica gel (2.5×20 cm) with dichloromethane:acetone (88:12). Solvent was removed and lyophilization yielded 2-amino-9-(2, 3-dideoxy-3-fluoro-β-D-erythro-pentofuranosyl)-6-(dimethylamino)-9H-purine 0.17 g (26%): mp 96°–100° C.; TLC $R_f$ 0.79 (silica gel, MeCN: 15N NH₄OH:H₂O/85:5:10);

$[\alpha]_D^{20}$ –17.6° (c=0.5, DMF);

UV $\lambda_{max}$ ($\epsilon \times 10^{-3}$) at pH 7,284 (15.6); at pH 13,284 (15.2);

¹H NMR (300 MHz, DMSO-d₆) δ7.96 (s, 1H, H₈), 6.24 (dd, 1H, ₁·, J=9.4 Hz, J=5.6 Hz), 5.84 (s, 2H, NH₂), 5.48 (t, 1H, OH₅·, J=5.8 Hz), 5.39 (dd, 1H, H₃·, J=53.8 Hz, J=4.2 Hz), 4.19 (dt, 1H, H₄·, J=27.4 Hz, J=4.4 Hz), 3.59 (t, 2H, H₅· and H₅··, J=5.0 Hz), 3.36 (b, 6H, N(CH₃)₂), 2.74–3.00 (m, 1H, H₂·), and 2.48–2.64 (m, 1H, H₂··);

MS (ci) 297 (M+1), 277 (M-F), 179 (MC₂—C₅H₈FO₂).

Elemental Analysis for C₁₂H₁₇FN₆O₂.0.40H₂O Calculated: C,47.49; H,5.91; F,6.26; N,27.69 Found: C,47.17; H,5.65; F,6.62; N,27.34

EXAMPLE 14

2-Amino-9-(2,3-dideoxy-3-fluoro-β-D-erythro-pentofuranosyl)-6-(propylamino)-9H-purine 2-Amino-6-propylamino-9H-purine was prepared by displacement of the chlorine group on 2-amino-6-chloropurine (Aldrich Chemical Company) by propylamine (Aldrich Chemical Company).

2-Amino-6-propylamino-9H-purine (0.50 g, 2.6 mmoles) and 2',3'-dideoxy-3'-fluorouridine (0.50 g, 2.2 mmoles) were suspended in 50 ml, 10 mM potassium phosphate buffer, pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 5 days, 192 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:acetone (9:1). Solvent was removed and lyophilization yielded 0.08 g of 2-amino-9-(2, 3-dideoxy-3-fluoro-β-D-erythro-pentofuranosyl)-6-(propylamino)-9H-purine (11%): mp 153° C.; TLC $R_f$ 0.60 (silica gel, MeCN:15N NH₄OH:H₂O/85:5:10);

$[\alpha]_D^{20}$ –6.40 (c=0.5, DMF);UV $\lambda_{max}$ ($\epsilon \times 10^{-3}$) at pH 7, 281 (13.8); at pH 13, 281 (13.7);¹H NMR (200 MHz, DMSO-d₆) δ7.94 (s, 1H, H₈), 6.24 (dd, 1H, H₁·, J=9.5 Hz, J=5.6 Hz) 7.34 (b, 1H, NH), 5.81 (b, 2H NH₂), 5.58 (m, 1H, OH₅·), 5.43 (dd, 1H, H₃·, J=53.7 Hz, J=4.1 Hz), 4.11–4.30 (m, 1H, H₄·), 3.61 (t, 2H, H₅· and H₅··, J=4.9 Hz), 3.4 (b, 2H, NCH₂), 2.56–3.10 (m, 2H, H₂· and H₂··), 1.53–1.64 (m, 2H), and 0.89 (t, 3H, CH₃, J=7.4 Hz); MS (ci) 311 (M+1), 291 (M-F), 193 (MH₂—C₅H₈FO₂). Anal. (C₁₃H₁₉FN₆O₂.0.20H₂O) C, H, F, N. Calculated (Found): C, 49.74 (49.96): H, 6.23 (6.11); F, 6.05 (5.84); N, 26.77 (26.41)

EXAMPLE 15

2-Amino-6-(cyclopropylmethoxy)-9-(2,3-dideoxy-3-fluoro-β-D-erythro-pentofuranosyl)-9H-purine 2-Amino-6-(cyclopropylmethoxy-9H-purine was prepared by displacement of the chlorine group on 2-amino-6-chloropurine (Aldrich Chemical Company) by cyclopropanemethanol (Aldrich Chemical Company) in the presence of sodium hydride.

2-Amino-6-(cycloropylmethoxy)-9H-purine (0.53 g, 2.6 mmoles) and 2',3'-dideoxy-3'-fluorouridine (0.50 g, 2.2 mmoles) were suspended in 50 ml, 10 mM potassium phosphate buffer, pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 4 days, 182 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone (9:1). Solvent was removed and lyophilization yielded 0.414 g of 2-amino-6-cyclopropylmethoxy-9-(2,3-dideoxy-3-fluoro-β-D-erythro-pentofuranosyl)-9H-purine (57%): mp 80°–81° C.; TLC $R_f$ 0.75 (silica gel, MeCN:15N $NH_4OH:H_2O$/85:5:10); $[\alpha]_D^{20}$ –19.0 (c=0.5, DMF);UV $\lambda_{max}$ ($\epsilon$×10$^{-3}$) at pH 7, 247 (9.7); at pH 13, 247 (9.3);$^1$H NMR (200 MHz, DMSO-d$_6$) δ8.13 (s, 1H, H$_8$), 6.47 (b, 2H, NH$_2$), 6.27 (dd, 1H, H$_{1'}$, J=9.3 Hz, J=5.6 Hz), 5.43 (dd, 1H, H$_{3'}$, J=54 Hz, J=4.2 Hz), 5.24 (t, 1H, OH$_{5'}$, J=5.6 Hz), 4.26 (d, 2H, OCH$_2$, J=7.2 Hz), 4.11–4.27 (m, 1H, H$_{4'}$), 3.59 (t, 2H, H$_{5'}$ and H$_{5''}$, J=5.2 Hz), and 2.62–3.01 (m, 2H, H$_{2'}$ and H$_{2''}$), 1.25–1.35, 0.55–0.64, and 0.35–0.40 (m, 5H, cyclopropyl group);

MS (ci) 324 (M+1), 304 (M-F), 206 (MH$_2$—C$_5$H$_8$FO$_2$). Anal. (C$_{14}$H$_{18}$FN$_5$O$_3$·0.25H$_2$O) C, H, F, N. Calculated (Found): C, 51.29 (50.96); H, 5.69 (5.43); F, 5.80 (5.56); N, 21.36 (20.99)

EXAMPLE 16

2-Amino-6-azetidinyl-9-(2,3-dideoxy-3-fluoro-β-D-erythro-pentofuranosyl-9H-purine 2-Amino-6-azetidinyl-9H-purine was prepared by displacement of the chlorine group on 2-amino-6-chloropurine (Aldrich Chemical Company) by azetidine (Aldrich Chemical Company).

2-Amino-6-azetidinyl-9H-purine (0.50 g, 2.6 mmoles) and 2',3'-dideoxy-3'-fluorouridine (0.71 g, 3.1 mmoles) were suspended in 50 ml, 10 mM potassium phosphate buffer, pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 7 days, 170 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:acetone (7:3). Fractions containing product were pooled, concentrated, and flash chromatographed a second time on silica gel (2.5×20 cm) with dichloromethane:methanol (96:4). Solvent was removed and lyophilization yielded 0.566 g of 2-amino-6-azetidinyl-9-(2,3 -dideoxy-3-fluoro-β-D-erythro-pentofuranosyl)-9H-purine (68%): mp 127°–129° C.; TLC $R_f$ 0.70 (silica gel, MeCN:15N NH$_4$OH:H$_2$O/85:5:10);

$[\alpha]_D^{20}$ –15.9 (c=0.51, DMF);UV $\lambda_{max}$ ($\epsilon$×10$^{-3}$) at pH 7, 285 (17.2); at pH 13, 285 (16.5);$^1$H NMR (300 MHz, DMSO-d$_6$) δ7.91 (s, 1H, H$_8$), 6.20 (dd, 1H, H$_{1'}$, J=9.4 Hz, J=5.6 Hz), 5.91 (b, 2H, NH$_2$), 5.46–5.49 (m, 1H, OH$_{5'}$), 5.38 (dd, 1H, H$_{3'}$, J=53.8 Hz, J=4.3 Hz), 4.12–4.35 (b, 5H, H$_{4'}$ and azetidinyl group), 3.5 (t, 2H, H$_{5'}$ and H$_{5''}$, J=4.9 Hz), 2.80–2.95 and 2.53–2.62 (m, 2H, H$_{2'}$ and H$_{2''}$), and 2.33–2.43 (m, 2H, azetidinyl group);

MS (ci) 309 (M+1), 289 (M-F), 191 (MH$_2$—C$_5$H$_8$FO$_2$). Anal. (C$_{13}$H$_{17}$FN$_6$O$_2$·0.65H$_2$O) C, H, F, N. Calculated (Found): C, 48.79 (48.87); H, 5.76 (5.37); F, 5.94 (6.26); N, 26.26 (25.89)

EXAMPLE 17

2-Amino-6-(4-methoxybenzylamino)-9-(2,3-dideoxy-3-fluoro-β-D-erythro-pentofuranosyl)-9H-purine 2-Amino-6-(4-methoxybenzylamino)-9H-purine was prepared by displacement of the chlorine group on 2-amino-6-chloropurine (Aldrich Chemical Company) by 4-methoxybenzylamine (Aldrich Chemical Company) in the presence of sodium hydride.

2-Amino-6-(4-methoxybenzylamino)-9H-purine (0.70 g, 2.6 moles) and 2',3'-dideoxy-3'-fluorouridine (0.50 g, 2.2 moles) were suspended in 50 ml, 10 mM potassium phosphate buffer, pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 7 days, 150 ml MeOH was added to the reaction. The reaction was applied to a column containing AG1-X2 (OH— form, 2.5×10 cm) and eluted with MeOH. Fractions containing produce were pooled, concentrated, and flash chromatographed on silica gel (2.5×20 cm) with dichloromethane:acetone (9:1). Solvent was removed and lyophilization yielded 0.338 g of 2-amino-6-(4-methoxybenzylamino)-9-(2,3-dideoxy-3-fluoro-β-D-erythro-pentofuranosyl)-9H-purine (48%): mp 194°–195° C.; TLC $R_f$ 0.70 (silica gel, MeCN:15N NH$_4$OH:H$_2$O/85:5:10);

$[\alpha]_D^{20}$ –14.5 (c=0.49, DMF); UV $\lambda_{max}$ ($\epsilon$×10$^{-3}$) at pH 7, 282 (18.7); at pH 13, 282 (18.2);$^1$H NMR (300 MHz, DMSO-d$_6$) δ7.94 (s, 1H, H$_8$), 7.27 (d, 2H, J=8.6 Hz), 6.85 (d, 2H, J=8.6 Hz), 6.22 (dd, 1H, H$_{1'}$, J=9.5 Hz, J=5.4 Hz) 5.85 (b, 1H, NH), 5.50–5.55 (m, 1H, OH$_{5'}$), 5.40 (dd, 1H, H$_{3'}$, J=53.6 Hz, J=4.4 Hz), 4.54 (b, 2H, NCH$_2$), 4.10–4.28 (m, 1H, H$_{4'}$). 3.71 (s, 3H, OCH$_3$) 3.58–3.60 (m, 2H, H$_{5'}$ and H$_{5''}$), and 2.78–2.98 and 2.52–2.59 (m, 2H, H$_{5'}$ and H$_{5''}$);

MS (ci) 389 (M+1), 369 (M-F), 271 (MH$_2$—C$_5$H$_8$FO$_2$). Anal. (C$_{18}$H$_{21}$FN$_6$O$_3$·0.05H$_2$O) C, H, F, N. Calculated (Found); C, 55.53 (55.24); H, 5.46 (5.44); F, 4.88 (4.89); N, 21.59 (21.23)

EXAMPLE 18

9-(2,3-dideoxy-3-fluoro-β-D-erythro-pentofuranosyl)-6-diethylamino-9H-purine

6-Diethylamino-9H-purine was prepared by displacement of the chlorine group on 6-chloropurine (Aldrich Chemical Company) by diethylamine (Aldrich Chemical Company).

6 Diethylamino-9H-purine (0.50 g, 2.6 mmoles) and 2',3'-dideoxy-3'-fluorouridine (0.72 g, 3.2 mmoles) were suspended in 50 ml, 10 mM potassium phosphate buffer, pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 11 days, 150 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:acetone (9:1). Solvent was removed and lyophilization yielded 0.372 g of 9-(2,3-dideoxy-3-fluoro-β-D-erythro-pentofuranosyl)-6-diethylamino- 9H-purine (46%): mp 114°–115° C.; TLC $R_f$ 0.70 (silica gel, MeCN:15N NH$_4$OH:H$_2$O/85:5:10);

$[\alpha]_D^{20}$ –22.6 (c=0.59, DMF);UV $\lambda_{max}$ ($\epsilon$×10$^{-3}$) at pH 7, 277 (21.1); at pH 13, 277 (20.7);$^1$H NMR (400 MHz, DMSO-d$_6$) δ8.32 and 8.17 (2s, 2H, H$_2$ and H$_8$), 6.38 (dd, 1H H$_1$·, J=9.1 Hz J=5.6 Hz), 5.55 (m, 1H, OH$_5$·), 5.41 (dd, 1H, H$_3$·, J=53.6 Hz, J=4.0 Hz), 4.22 (dt, 1H, H$_4$·, J=27.0 Hz, J=3.8 Hz), 3.65–4.15 (b, 4H, CH$_3$CH$_2$NCH$_2$CH$_3$), 3.58–3.60 (m, 2H, H$_5$· and H$_5$··) 2.85–3.06 and 2.55–2.70 (m, 2H, H$_2$· and H$_2$··), and 1.17 (t, 6H, CH$_3$CH$_2$NCH$_2$CH$_3$), J=6.6 Hz);

MS (ci) 310 (M+1), 290 (M-F), 192 (MH$_2$—C$_5$H$_8$FO$_2$). Anal. (C$_{14}$H$_{20}$FN$_5$O$_2$·0.05H$_2$O) C, H, F, N. Calculated (Found): C, 54.36 (54.03); H, 6.52 (6.37); F, 6.14 (6.05); N, 22.64 (22.35)

EXAMPLE 19

6-Propylamino-9-(2,3-dideoxy-3-fluoro-β-D-erythro-pentofuranosyl)-9H-purine

6-Propylamino-9H-purine was prepared by displacement of the chlorine group on 6-chloropurine (Aldrich Chemical Company) by propylamine (Aldrich Chemical Company).

6 Propylamino-9H-purine (0.46 g, 2.6 mmoles) and 2',3'-dideoxy-3'-fluorouridine (0.50 g, 2.2 mmoles) were suspended in 50 ml, 10 mM potassium phosphate buffer, pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 5 days, 150 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:acetone (9:1). Solvent was removed and lyophilization yielded 0.14 g of 6-propylamino-9-(2,3-dideoxy-3-fluoro-β-D-erythro-pentofuranosyl)- 9H-purine (22%): mp 114°–115° C.; TLC R$_f$ 0.75 (silica gel, MeCN:15N NH$_4$OH:H$_2$O/85:5:10);

[α]$_D^{20}$–22.2 (c=0.50, DMF);UV λ$_{max}$ (ϵ×10$^{-3}$) at pH 7, 267 (17.8); at pH 13, 267 (18.1);$^1$H NMR (400 MHz, DMSO-d$_6$) 8.32 and 8.18 (2s, 2H, H$_2$ and H$_8$), 7.92 (b, 1H, NH), 6.38 (dd, 1H H$_1$·, J=9.3 Hz J=5.6 Hz), 5.52 (m, 1H, OH$_5$·), 5.42 (dd, 1H, H$_3$·, J=53.6 Hz, J=4.4 Hz), 4.23 (dm, 1 Hm H$_4$·, J=27.2 Hz), 3.58–3.62 (m, 2H, H$_5$· and H$_5$··), 3.40–3.42 (m, 2H, NCH$_2$CH$_2$CH$_3$) 2.90–3.10 (m, 1H, H$_2$·) 2.56–2.68 (m, 1H, H$_2$··), 1.55–1.60 (m, 2H, NCH$_2$CH$_2$CH$_3$), and 0.87 (t, 3H, NCH$_2$CH$_2$CH$_3$, J=7.4 Hz); MS (ci) 296 (M+1), 276 (M-F), 178 (MH$_2$—C$_5$H$_8$FO$_2$).

Anal. (C$_{13}$H$_{18}$FN$_5$O$_2$) C, H, F, N. Calculated (Found): C, 52.87 (52.94); H, 6.14 (6.03); F, 6.43 (6.08); N, 23.71 (23.43).

EXAMPLE 20

9-(2,3-dideoxy-3-fluoro-β-D-erythro-pentofuranosyl)-6-ethylmethylamino-9H-purine 6-Ethylmethylamino-9H-purine was prepared by displacement of the chlorine group on 6-chloropurine (Aldrich Chemical Company) by N-ethylmethylamine (Aldrich Chemical Company).

6 Ethylmethylamino-9H-purine (0.46 g, 2.6 mmoles) and 2',3'-dideoxy-3'-fluorouridine (0.50 g, 2.2 moles) were suspended in 50 ml, 10 mM potassium phosphate buffer, pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 6 days, 150 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:acetone (9:1). Solvent was removed and lyophilization yielded 0.323 g of 9-(2,3-dideoxy-3-fluoro-β-D-erythro-pentofuranosyl)-6-ethylmethylamino- 9H-purine (50%): mp 99°–100° C.;TLC R$_f$ 0.75 (silica gel, MeCN:15N NH$_4$OH:H$_2$O/85:5:10);

[α]$_D^{20}$–22.8 (c=0.50, DMF);UV λ$_{max}$ (ϵ×10$^{-3}$) at pH 7, 275 (19.2); at pH 13, 275 (19.4);$^1$H NMR (400 MHz, DMSO-d$_6$) δ8.35 and 8.20(2s, 2H, H$_2$ and H$_8$), 6.40 (dd, 1H H$_1$·, J=9.3 Hz J=5.6 Hz), 5.45–5.50 (m, 1H, OH$_5$·), 5.41 (dd, 1H, H$_3$·, J=53.6 Hz, J=4.6 Hz), 4.23 (dt, 1H, H$_4$·, J=27.1 Hz, J=4.4 Hz), 4.10 (b, 2H NCH$_2$), 3.49–3.59 (m, 2H, H$_5$· and H$_5$··).3.3(b, 3H, NCH$_3$), 2.90–3.10 and 2.49–2.68 (m, 2H, H$_2$· and H$_2$··), and 1.14 (t, 3H, CH$_3$, J=7.0 Hz);

MS (ci) 296 (M+1), 276 (M-F), 178 (MH$_2$—C$_5$H$_8$FO$_2$). Anal. (C$_{13}$H$_{18}$FN$_5$O$_2$) C, H, F, N. Calculated (Found): C, 52.87 (52.95); H, 6.14 (6.06); F, 6.43 (6.36); N, 23.11 (23.61)

EXAMPLE 21

2-Amino-9-(2,3-dideoxy-3-fluoro-β-D-erythro-pentofuranosyl)-6-phenylamino-9H-purine 2-Amino-6-phenylamino-9H-purine was prepared by displacement of the chlorine group on 2-amino-6-chloropurine (Aldrich Chemical Company) by aniline (Aldrich Chemical Company).

2-Amino-6-phenylamino-9H-purine (0.63 g, 2.7 mmoles) and 2',3'-dideoxy-3'-fluorouridine (0.50 g, 2.2 mmoles) were suspended in 50 ml, 10 mM potassium phosphate buffer, pH 7.0, containing 0.04% potassium azide. Purine nucleoside phosphorylase (1120 I.U.) and thymidine phosphorylase (10,000 I.U.) (Krenitsky et al., *Biochemistry*, 20, 3615 (1981) and U.S. Pat. No. 4,381,344) immobilized on DEAE cellulose was added to the reaction and the suspension was stirred at 45° C. After 2 days, 100 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:acetone:methanol (97:2:1). Fractions containing product were combined and flash chromatographed on a second silica gel column (2.5×20 cm) with hexane:acetone (6:4). Solvent was removed and lyophilization yielded 0.364 g of 2-amino-9-(2,3-dideoxy-3-fluoro-β-D-erythro-pentofuranosyl)-6-phenylamino-9H-purine (49%): mp 193°–194° C.;

UV λ$_{max}$(ϵ×10$^-$) at pH 7, 303 (23.0) and 251 (13.6); at pH 13, 303 (22.2) and 251 (13.20); $^1$H NMR (300 MHz, DMSO-d$_6$) δ9.44 (s, 1H, NH), 8.09 (s, 1H, H$_8$), 8.01 (d, 2H phenyl group, J=7.6) 7.25–7.30 (m, 2H, phenyl group), 6.98 (t, 1H, phenyl group, J=7.4 Hz), 6.27 (dd, 1H, H$_1$·, J=9.3 Hz, J=5.6 Hz), 6.18(s, 2H, NH$_2$), 5.42 (dd, 1H, H$_3$·, J=53.7 Hz, J=4.3 Hz), 5.38 (t, 1H, OH$_5$·, J=5.7 Hz,), 4.20 (dt, 1H, H$_4$·, J=27.0 Hz, J=4.6 Hz), 3.61 (t, 2H, H$_5$· and H$_5$··, J=5.1 Hz),2.80–3.06 and 2.53–2.69 (2m, 2H, H$_2$· and H$_2$··);

MS (ci) 345 (M+1), 325 (M-F), 227 (MH$_2$—C$_5$H$_8$FO$_2$). Anal. (C$_{16}$H$_{17}$FN$_6$O$_2$) C, H, F, N. Calculated (Found): C, 55.81 (55.76); H, 4.98 (4.97); F, 5.52 (5.38); N, 24.41 (24.20)

EXAMPLE 22

9-(2,3-Dideoxy-3-fluoro-β-D-erythro-pentofuranosyl)-6-morpholino-9H-purine

6-Morpholino-9H-purine was prepared by displacement of the chlorine group on 6-chloropurine (Aldrich Chemical Company) by morpholine (Aldrich Chemical Company).

6-Morpholino-9H-purine (0.50 g, 2.4 mmoles) and 2',3'-dideoxy-3'-fluorouridine (0.67 g, 2.9 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., Biochemistry, 20, 3615, 1981 and U.S. Pat. No. 4,381,344) immobilized on DEAE cellulose was added to the reaction and the suspension was stirred at 45° C. After 9 days, 140 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone (9:1). Solvent was removed and lyophilization yielded 0.396 g of 9-(2,3-dideoxy-3-fluoro-β-D-erythro-pentofuranosyl)-6-morpholino-9H-purine (50%): mp 175°–178° C.; $[\alpha]_D^{20}$ −20.2 (c=0.51, DMF); UV $\lambda_{max}$ (ε×10$^{-3}$) at pH 7, 278 (21.4); at pH 13, 278 (21.1); $^1$H NMR (400 MHz, DMSO-d$_6$) δ8.40 and 8.25 (2s, 2H, H$_2$ and H$_8$) 6.41 (dd, 1H, H$_{1'}$, H=9.3 Hz, J=5.7 Hz), 5.43 (dd, 1H, H$_{3'}$, J=53.6 Hz, J=4.4 Hz), 5.40 (m, 1H, OH$_{5'}$), 4.10–4.30 (b, 5H, H$_{4'}$ and morpholino group), 3.60 (m, 2H, H$_{5'}$ and H$_{5''}$), and 2.88–3.04 and 2.59–2.69 (m, 2H, H$_{2'}$ and H$_{2''}$); MS (ci) 324 (M+1), 304 (M-F), 206 (MH$_2$—C$_5$H$_8$FO$_2$).

Anal. (C$_{14}$H$_{18}$FN$_5$O$_3$) C, H, F, N. Calculated (Found): C, 52.01 (52.26); H, 5.61 (5.68); F, 5.88 (5.61); N, 21.66 (21.27).

EXAMPLE 23

9-(2,3-Dideoxy-3-fluoro-β-D-erythro-pentofuranosyl)-6-dimethylamino-9H-purine

6-Dimethylamino-9H-purine (0.42 g, 2.6 mmoles), (Aldrich Chemical Company) and 2',3'-dideoxy-3'-fluorouridine (0.50 g, 2.2 moles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., Biochemistry, 20, 3615, 1981 and U.S. Pat. No 4,381,344) immobilized on DEAE cellulose was added to the reaction and the suspension was stirred at 45° C. After 6 days, 172 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone (92:8). Solvent was removed and lyophilization yielded 0.341 g of 9-(2,3-dideoxy-3-fluoro-β-D-erythro-pentofuranosyl)-6-dimethylamino-9H-purine (55%): mp 105°–107° C.; $[\alpha]_D^{20}$ −23.3 (c=0.52, DMF); UV $\lambda_{max}$ (ε×10$^{-3}$) at pH 7, 275 (25.1); at pH 13, 274 (18.4); $^1$H NMR (300 MHz, DMSO-d$_6$) δ8.35 and 8.20 (2s, 2H, H$_2$ and H$_8$), 6.40 (dd, 1H, H$_{1'}$, J=9.3 Hz, J=5.6 Hz), 5.46 (t, 1H, OH$_{5'}$, J=5.7 Hz), 5.43 (dd, 1H, H$_{3'}$, J=53.8 Hz, J=4.5 Hz), 4.22 (dt, 1H, H$_{4'}$, J=27.1 Hz, J=4.4 Hz), 3.58–3.61 (m, 2H, H$_{5'}$ and H$_{5''}$), 3.43 (b, 6H, CH$_3$NCH$_3$), and 2.82–3.10 and 2.55–2.70 (m, 2H, $_{2'}$ and H$_{2''}$); MS (ci) 282 (M+1), 262 (M-F), 164 (MH$_2$—C$_5$H$_8$FO$_2$).

Anal. (C$_{12}$H$_{16}$FN$_5$O$_{x2}$·0.15H$_2$O) C, H, F, N. Calculated (Found): C, 50.75 (50.43); H, 5.78 (5.72); F, 6.69 (6.40); N, 24.66 (24.35).

EXAMPLE 24

2-Amino-6-(cyclopropylmethoxy)-9-(2,3-dideoxy-3-fluoro-β-D-erythro-pentofuranosyl)-9H-purine 2-Amino-6-(cyclopropylmethoxy)-9H-purine was prepared by displacement of the chlorine group on 2-amino-6-chloropurine (Aldrich Chemical Company) by cyclopropanemethanol (Aldrich Chemical Company) in the presence of sodium hydride.

2-Amino-6-(cyclopropylmethoxy)-9H-purine (0.53 g, 2.6 mmoles) and 2',3'-dideoxy-3'-fluorouridine (0.50 g, 2.2 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., Biochemistry, 20, 3615, 1981 and U.S. Pat. No. 4,381,344) immobilized on DEAE cellulose was added to the reaction and the suspension was stirred at 45° C. After 4 days, 182 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone (9:1). Solvent was removed and lyophilization yielded 0.414 g of 2-amino-6-(cyclopropylmethoxy)-9-(2,3-dideoxy-3-fluoro-β-D-erythro-pentofuranosyl)-9H-purine (57%): mp 80°–81° C.; TLC R$_f$ 0.75 (silica gel, MeCN:15N NH$_4$OH:H$_2$O/85:5:10); $[\alpha]_D^{20}$ −19.0 (c=0.5, DMF); UV $\lambda_{max}$ (ε×10$^{-3}$) at pH 7, 247 (9.7); at pH 13, 247 (9.3), $^1$H NMR (200 MHz, DMSO-d$_6$) δ8.13 (s, 1H, H$_8$), 6.47 (b, 2H, NH$_2$), 6.27 (dd, 1H, H$_{1'}$, J=9.3 Hz, J=5.6 Hz), 5.43 (dd, 1H, H$_{3'}$, J=54 Hz, J=4.2 Hz), 5.24 (t, 1H, OH$_{5'}$, J=5.6 Hz), 4.26 (d, 2H, OCH$_2$, J=7.2 Hz), 4.11–4.27 (m, 1H, H$_{4'}$), 3.59 (t, 2H, H$_{5'}$ and H$_{5''}$, J=5.2 Hz), and 2.62–3.01 (m, 2H, H$_{2'}$ and H$_{2''}$), and 1.25–1.35, 0.55–0.64, and 0.35–0.40 (m, 5H, cyclopropyl group); MS (ci) 324 (M+1), 304 (M-F), 206 (MH$_2$—C$_5$H$_8$FO$_2$).

Anal. (C$_{14}$H$_{18}$FN$_5$O$_3$·0.25H$_2$O) C, H, F, N. Calculated (Found): C, 51.29 (50.96); H, 5.69 (5.43); F, 5.80 (5.56); N, 21.36 (20.99).

EXAMPLE 25

9-(2,3-Dideoxy-3-fluoro-β-D-erythro-pentofuranosyl)-6-(hexylthio)-9H-purine

6-Hexylthio-9H-purine (0.59 g, 2.5 mmoles) (Alfred Bader Division of Aldrich Chemical Company) and 2',3'-dideoxy-3'-fluorouridine (0.70 g, 3.0 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., Biochemistry, 20, 3615, 1981 and U.S. Pat. No. 4,381,344) immobilized on DEAE cellulose was added to the reaction and the suspension was stirred at 45° C. After 7 days, 193 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone (95:5). Solvent was removed and lyophilization yielded 0.53 g of 9-(2,3-dideoxy-3-fluoro-β-D-erythro-pentofuranosyl)-6-hexylthio-9H -purine (59%): mp 46°–49° C.; TLC R$_f$ 0.75 (silica gel, MeCN:15N NH$_4$OH:H$_2$O/85:5:10); $[\alpha]_D^{20}$ −17.8 (c=0.5, DMF); UV $\lambda_{max}$ (ε×10$^{-3}$) at pH 7, 293 (20.4); at pH 13, 293 (20.4); $^1$ NMR (200 MHz, DMSO-d$_6$) δ8.75 and 8.69 (2s, 2H, H$_2$ and $_8$), 6.50 (dd, 1H, H$_{1'}$, J=8.9 Hz), J=5.8 Hz), 5.49 (dd, 1H, H$_{3'}$, J=53.2 Hz), J=4.4 Hz), 5.23 (t, 1H, OH$_{5'}$, J=5.4 Hz), 4.18–4.38 (m, 1H, H$_{4'}$), 3.63 (t, 2H, H$_{5'}$ and H$_{5''}$, J=5.2 Hz), 3.34 (t, 2H, sCH$_2$, J=7.2 Hz), 2.54–3.00 (m, 2H, H$_2$, and H$_{2''}$), 1.62–1.74, 1.23–1.44, and 0.81–0.88 (m, 11H); MS (ci) 355 (M+1), 335 (M-F), 237 (MH$_2$—C$_5$H$_8$FO$_2$).

Anal. (C$_{16}$H$_{23}$FN$_4$O$_2$S) C, H, F, N, S. Calculated (Found): C, 54.22 (54.21); H, 6.54 (6.51); F, 5.36 (5.13); N, 15.81 (15.77); S, 9.05 (9.23).

EXAMPLE 26

2-Amino-9-(2,3-dideoxy-3-fluoro-β-D-erythro-pentofuranosyl)-6-(propylamino)-9H-purine 2-Amino-6-propylamino-9H-purine was prepared by displacement of the chlorine group on 2-amino-6-chloropurine (Aldrich Chemical Company) by propylamine (Aldrich Chemical Company).

2-Amino-6-propylamino-9H-purine (0.50 g, 2.6 mmoles) and 2',3'-dideoxy-3'-fluorouridine (0.50 g, 2.2 mmoles) were suspended in 50 ml 10 mM potassium phosphate buffer, pH 7.0, containing 0.4% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added to the reaction and the suspension was stirred at 45° C. After 5 days, 192 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone (9:1). Solvent was removed and lyophilization yielded 0.08 g of 2-amino-9-(2,3-dideoxy-3-fluoro-β-D-erythro-pentofuranosyl)-6-(propylamino)-9H-purine (11%): mp 153° C.; TLC R$_f$ 0.60 (silica gel, MeCN:15N NH$_4$OH@H$_2$O/85:5:10); [α]$_D^{20}$ −6.40 (c=0.5, DMF); UV λ$_{max}$ (ε×10$^{-3}$) at pH 7, 281 (13.8); at pH 13, 281 (13.7); $^1$H NMR (200 MHz, DMSO-d$_6$) δ7.94 (s, 1H, H$_8$), 6.24 (dd, 1H, H$_{1'}$, J=9.5 Hz, J=5.6 Hz), 7.34 (b, 1H, NH), 5.81 (b 2H, NH$_2$), 5.58 (m, 1H, OH$_5'$), 5.43 (dd, 1H, H$_{3'}$, J=53.7 Hz, J=4.1 Hz), 4.11–4.30 (m, 1H, H$_{4'}$), 3.61 (t, 2H, H$_5'$ and H$_{5''}$, J=4.9 Hz), 3.4 (b, 2H, NCH$_2$), 2.56–3.10 (m, 2H, H$_2$, and H$_{2''}$), 1.53–1.64 (m, 2H), and 0.89 (t, 3H, CH$_3$, J=7.4 Hz); MS (ci) 311 (M+1), 291 (M-F), 193 (MH$_2$—F$_5$H$_8$FO$_2$).

Anal. (C$_{13}$H$_{19}$FN$_6$O$_2$·0.20H$_2$O), C, H, F, N. Calculated (Found): C, 49.74 (49.96); H, 6.23 (6.11); F, 6.05 (5.84); N, 26.77 (26.41).

EXAMPLE 27

6-Anilino-9-(2,3-dideoxy-3-fluoro-β-D-erythro-pentofuranosyl)-9H-purine

6-Anilino-9H-purine was prepared by displacement of the chlorine group on 6-chloropurine (Aldrich Chemical Company) by aniline (Aldrich Chemical Company).

6-Anilino-9H-purine (0.55 g 2.6 mmoles) and 2',3'-dideoxy-3'-fluorouridine (0.50 g, 2.2 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added to the reaction and the suspension was stirred at 45° C. After 4 days, 180 ml MeOH was added to the reaction. The reaction was applied to a column containing AG1-X2 (OH— form, 2.5×10 cm) and eluted with MeOh. Fractions containing product were pooled, concentrated, and flash chromatographed on silica gel (2.5×20 cm) with dichloromethane:acetone (93:7). Solvent was removed and lyophilization yielded 0.323 g of 6-anilino-9-(2,3-dideoxy-3-fluoro-β-D-erythro-pentofuranosyl)-9H-purine (45%): mp 83° C.; TLC R$_f$ 0.72 (silica gel, MeCN:15N NH$_4$OHiH$_2$O/85:5:10); [α]$_D^{20}$ −18.8 (c=0.5, DMF); UV λ$_{max}$ (ε×10$^{-3}$) at pH 7,288 (22.2); at pH 13, 288 (21.0); $^1$H NMR (300 MHz, DMSO-d$_6$) δ9.98 (s, 1H, NH), 8.54 and 8.41 (2s, 2H, H$_2$ and H$_8$), 7.95 (d, 2H, J=7.6 Hz), 7.31–7.37 (m, 2H), 7.06 (t, 1H, J=7.4 Hz), 6.48 (dd, 1H, H$_{1'}$, J=9.2 Hz, J=5.7 Hz), 5.38–5.58 (m, 2H, OH$_5'$, and H$_{3'}$), 4.28 (dt, 1H, H$_{4'}$, J=26.8 Hz, J=4.6 Hz) 3.65 (m, 2H, H$_{5'}$ and H$_{5''}$), and 2.97–3.18 and 2.64–2.78 (m, 2H, H$_2$, and H$_{2''}$); MS (ci) 330 (M+1), 310 (M-F), 212 (MH$_2$—C$_5$H$_8$FO$_2$).

Anal. (C$_{16}$H$_{16}$FN$_5$O$_2$) C, H, F, N. Calculated (Found): C, 58.35 (58.13); H, 4.90 (4.87); F, 5.77 (5.48); N, 21.27 (20.98).

EXAMPLE 28

9-(2,3-Dideoxy-3-fluoro-β-D-erythro-pentofuranosyl)-6-(methylamino)-9H-purine

6-Methylamino-9H-purine (0.41 g, 2.7 moles) (Sigma Chemical Company) and 2',3'-dideoxy-3'-fluorouridine (0.50 g, 2.2 moles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added to the reaction and the suspension was stirred at 45° C. After 2 days, 150 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone (6:4). Solvent was removed and lyophilization yielded 0.45 g of 9-(2,3-dideoxy-3-fluoro-β-D-erythro-pentofuranosyl)-6-(methylamino)-9H-purine (73%): mp 100°–103° C.; TLC R$_f$ 0.69 (Silica gel, MeCN:15N NH$_4$OH:H$_2$O/85:5:10); [α]$_D^{20}$ −23.8° C. (c=0.5, DMF); UV λ$_{max}$ (ε×10$^{-3}$) at pH 7, 265 (15.6); at pH 13, 265 (16.0); $^1$H NMR (300 MHz, DMSO-d$_6$) δ8.34 and 8.24 (2s, 2H, H$_2$ and H$_8$), 7.86 (b, 1H, NH), 6.41 (dd, 1H, H$_{1'}$, J=9.3 Hz, J=5.6 Hz), 5.37–5.37 and 5.52–5.56 (2m, 2H, OH$_5'$, and H$_{3'}$), 4.25 (dt, 1H, H$_{4'}$, J=27.0 Hz, J=4.2 Hz), 3.60–3.64 (m, 2H, H$_{5'}$ and H$_{5''}$), 3.03–3.16 (m, 1H, H$_{2'}$), 2.92–2.99 (b, 3H, CH$_3$), and 2.57–2.74 (m, 1H, H$_{2''}$); MS (ci) 268 (M+1), 248 (M-F), 150 (MH$_2$C$_5$H$_8$FO$_2$).

Anal. (C$_{11}$H$_{14}$FN$_5$O$_2$), C, H, F, N. Calculated (Found): C, 47.36 (47.60); H, 5.53 (5.26); F, 6.81 (6.57); N, 25.10 (24.87).

EXAMPLE 29

2-Amino-6-benzylmercapto-9-(2,3-dideoxy-3-fluoro-β-D-erythro-pentofuranosyl-9H-purine 2-Amino-6-benzylmercapto-9H-purine (0.70 g, 2.7 mmoles) and 2',3'-dideoxy-3'-fluorouridine (0.50 g, 2.2 mmoles) were suspended in 50 ml 10 mM potassium phosphate buffer, pH 6.8, containing 0.04% potassium azide. Purine nucleoside phosphorylase (1120 I.U.) and thymidine phosphorylase (10,000 I.U.) immobilized on DEAE cellulose was added to the reaction and the suspension was stirred at 45° C. After 2 days, 200 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:methanol (95:5). Fractions containing products were pooled, concentrated, and further chromatographed on silica gel (2.5×20 cm) with ethyl acetate:hexane (1:1). Solvent was removed and lyophilization yielded 0.175 g of 2-amino-6-benzylmercapto-9-(2,3-dideoxy-3-fluoro-β-D-erythro-pentofuranosyl)-9H-purine (21%): mp 150°–151° C.; $[\alpha]_D^{20}$ −20.8 (c=0.50 DMF); UV $\lambda_{max}$ ($\epsilon \times 10^{-3}$) at pH 7, 247 (14.0) and 312 (14.0); at pH 13, 247 (13.6) and 312 (13.8); $^1$H NMR (300 MHz, DMSO-d$_6$) δ8.18 (s, 1H, $_8$), 7.47 and 7.27 (2m, 5H, C$_6$H$_5$), 6.83 (b, 2H, NH$_2$), 6.26 (dd, 1H, H$_{1'}$, J=9.2 Hz, J=5.8 Hz), 5.42 (dd, 1H, H$_{3'}$, J=53.7 Hz, J=4.3 Hz), 5.17 (t, 1H, OH$_{5'}$, J=5.6 Hz), 4.55 (s, 2H, SCH$_2$), 4.18 (dt, 1H, H$_{4'}$, J=26.7 Hz, J=4.9 Hz), 3.57 (t, 2H, H$_{5'}$ and H$_{5''}$, J=5.2 Hz), 2.91 and 2.62 (2m, 2H, H$_{2'}$ and H$_{2''}$); MS (ci) 376 (M+1), 356 (M-F), 258 (MH$_2$—C$_5$H$_8$FO$_2$).

Anal. (C$_{17}$H$_{18}$FN$_5$O$_2$S) C, H, F, N, S. Calculated (Found): C, 54.39 (54.33); H, 4.83 (4.82); F, 5.06 (4.88); N, 18.65 (18.32); S, 8.54 (8.61).

EXAMPLE 30

2-Amino-6-benzylamino-9-(2,3-dideoxy-3-fluoro-β-D-erythro-pentofuranosyl)-9H-purine 2-Amino-6-benzylamino-9H-purine was prepared by displacement of the chlorine group on 2-amino-6-chloropurine (Aldrich Chemical Company) by benzylamine (Aldrich Chemical Company).

2-Amino-6-benzylamino-9H-purine (0.64 g, 2.7 mmoles) and 2',3'-dideoxy-3'-florouridine (0.50 g, 2.2 mmoles) were suspended in 50 ml 10 mM potassium phosphate buffer containing 0.04% potassium azide. After the pH was adjusted to 7.0, purified purine nucleoside phosphorylase (15,700 I.U.) and thymidine phosphorylase (4,000 I.U.) (Krenitsky, et al., *Biochemistry*, 20, 3615, 1981 and U.S. Pat. No. 4,381,344) were added to the reaction and the suspension was stirred at 45° C. After 24 hours, purine nucleoside phosphorylase (1120 I.U.) and thymidine phosphorylase immobilized onto 10 ml of DEAE-cellulose were added. After an additional two days, 150 ml of methanol was added to the reaction. The reaction was filtered through Celite and the filtrate was applied to an ionic exchange column (AG1-X2, 2.5×10 cm, OH— form). After eluting the product with methano, fraction were combined and concentrated. The residue was then purified by flash chromatography on silica gel (5×20 cm column) with dichloromethane:methanol (95:5). Solvent was removed and lyophilization yielded 0.42 g of 2-amino-6-benzylamino-9-(2,3-dideoxy-3-fluoro-β-D-erythro-pentofuranosyl)-9H-purine (54%): mp 90°–94° C.; $[\alpha]_D^{20}$ −16.2 (c=0.5, DMF); UV $\lambda_{max}$ ($\epsilon \times 10^{-3}$) at pH 7, 282 (17.5); at pH13, 282 (17.7); $^1$H NMR (300 MHz, DMSO-d$_6$) δ7.95 (s, 1H, H$_8$), 7.93 (b, 1H, NH), 7.28 (m, 5H, C$_6$H$_5$), 6.23 (dd, 1H, H$_{1'}$, J=9.4 Hz, J=5.6 Hz), 5.87 (b, 2H, NH$_2$), 5.54 (t, 1H, OH$_{5'}$, J=5.7 Hz), 5.40 (dd, 1H, H$_{3'}$, J=53.7 Hz, J=4.2 Hz), 4.68 (b, 2H, CH$_2$), 4.19 (dt, 1H, H$_{4'}$, J=27.2 Hz, J=4.4 Hz), 3.60 (m, 2H, H$_{5'}$ and H$_{5''}$), 2.90 and 2.58 (m, 2H, H$_{2'}$ and H$_{2''}$); MS (ci) 359 (M+1), 339 (M-F), 241 (MH$_2$—C$_5$H$_8$FO$_2$).

Anal. (C$_{17}$H$_{19}$FN$_6$O$_2$.0.25$_2$O) C, H, F, N. Calculated (Found): C, 56.27 (56.57); H, 5.42 (5.30); F, 5.24 (5.00); N, 23.16 (22.80).

EXAMPLE 31

2-Amino-9-(2,3-dideoxy-3-fluoro-β-D-erythro-pentofuranosyl)-6-hexylamino-9H-purine 2-Amino-6-hexylamino-9H-purine was prepared by displacement of the chlorine group on 2-amino-6-chloropurine (Aldrich Chemical Company) by hexylamine (Aldrich Chemical Company).

2-Amino-6-hexylamino-9H-purine (0.63 g, 2.6 mmoles) and 2',3'-dideoxy-3'-fluorouridine (0.50 g, 2.2 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added to the reaction and the suspension was stirred at 45° C. After 9 days, 150 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone:methanol/97:2:1. Solvent was removed and lyophilization yielded 0.48 g of 2-amino-9(2, 3-dideoxy-3-fluoro-β-D-erythro-pentofuranosyl)-6-hexylamino-9H-purine (61%): mp 50°–51° C.; TLC R$_f$ 0.86 (silica gel, MeCN:15N NH$_4$OH:H$_2$O/85:5:10); $[\alpha]_D^{20}$ −13.2° (c=0.5, DMF); UV $\lambda_{max}$ ($\epsilon \times 10^{-3}$) at pH 7, 281 (15.4); at pH 13, 281 (15.4); $^1$H NMR (400 MHz, DMSO-d$_6$) δ7.89 (s, 1H, H$_8$), 7.30 (b, 1H, NH), 6.19 (dd, 1H, H$_{1'}$, J=9.7 Hz, J=5.6 Hz), 5.77 (b, 2H, NH$_2$), 5.56 (m, 1H, OH$_{5'}$), 5.38 (dd, 1H, H$_{3'}$, J=53.7 Hz, J=4.2 Hz), 4.17 (dm, 1H, H$_{4'}$, J=27.5 Hz, 3.57 (t, 2H, H$_{5'}$ and H$_{5''}$, J=5.0 Hz, 3.35 (b, 2H, NCH$_2$CH$_2$ (CH$_2$)$_3$CH$_3$), 2.78–2.97 and 2.47–2.60 (m, 2H, H$_{2'}$ and H$_{2''}$) 1.52 (m, 2H, NCH$_2$CH$_2$(CH$_2$)$_3$CH$_3$), 1.27 (b, 6H, NCH$_2$CH$_2$(CH$_2$)$_3$CH$_3$), and 0.84 (t, 3H, NCH$_2$CH$_2$(CH$_2$)$_3$CH$_3$, J=6.8 Hz); MS (ci) 353 (M+1), 333 (M-F), 235 (MH$_2$—C$_5$H$_8$FO$_2$).

Anal. (C$_{16}$H$_{25}$FN$_6$O$_2$.0.50H$_2$O), C, H, F, N. Calculated (Found): C, 53.17 (53.40); H, 7.25 (6.95); F, 5.26 (5.22); N, 23.25 (23.28).

EXAMPLE 32

9-(2,3-Dideoxy-3-fluoro-β-D-erythro-pentofuranosyl)-6-propylthio-9H-purine

6-Propylthio-9H-purine (0.50 g, 2.6 mmoles) (Alfred Bader Division of Aldrich Chemical Company) and 2',3'-dideoxy-3'-fluorouridine (0.50 g, 2.2 mmoles) were suspended in 500 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added to the reaction and the suspension was stirred at 45° C. After 4 days, 175 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (2.5×20 cm) with dichloromethane:acetone (9:1). The product was then further chromatographed on silica gel (2.5×20 cm) with dichloromethane:acetone (98:2). Solvent was removed and lyophilization yielded 0.27 g of 9-(2,3-dideoxy-3-fluoro-β-D-erythro-pentofuranosyl)-6-propylthio-9H-purine (39%): mp 85°–86° C.; TLC R$_f$ 0.87 (silica gel, MeCN:15N NH$_4$OH:H$_2$O/85:5:10); $[\alpha]_D^{20}$ −20.2° (c=0.5, DMF); UV $\lambda_{max}$ ($\epsilon \times 10^{-3}$) at pH 7, 293 (20.0); at pH 13, 292 (20.4); $^1$H NMR (300 MHz, DMSO-d$_6$) δ8.74 and 8.68 (2s, 2H, H$_2$ and H$_8$), 6.48 (dd, 1H, H$_{1'}$, J=9.0 Hz, J=5.8 Hz), 5.46 (dd, 1H, H$_{3'}$, J=53.4 Hz, J=4.2 Hz), 5.21 (t, 1H, OH$_{5'}$, J=5.6 Hz), 4.26 (dt, 1H, H$_{4'}$, J=26.2 Hz, J=4.8 Hz), 3.59–3.62 (m, 2H, H$_{5'}$ and H$_{5''}$), 3.25 (b, 2H, SCH$_2$CH$_2$CH$_3$), 2.95–3.20 and 2.62–2.80 (2m, 2H, H$_{2'}$ and H$_{2''}$), 1.69–1.76 (m, 2H, SCH$_2$CH$_2$CH$_3$) and 1.00 (t, 3H, SCH$_2$CH$_2$CH$_3$, J=7.4 Hz); MS (ci) 313 (M+1), 293 (M-F), 195 (MH$_2$—C$_5$H$_8$FO$_2$).

Anal. (C$_{13}$H$_{17}$FN$_4$O$_2$S) C, H, F, N, S. Calculated (Found): C, 49.99 (49.87); H, 5.49 (5.49); F, 6.08 (6.09); N, 17.94 (17.66); S, 1026 (10.19).

EXAMPLE 33

2-Amino-9-(2,3-dideoxy-3-fluoro-β-D-erythro-pentofuranosyl)-6-(4-methoxyanilino)-9H-purine 2-Amino-6-(4-methoxyanilino)-9H-purine was prepared by displacement of the chlorine group on 2-amino-6-chloropurine (Aldrich Chemical Company) by anisidine (Aldrich Chemical Company).

2-Amino-6-(4-methoxyanilino)-9H-purine (0.72 g, 2.6 mmoles) and 2',3'-dideoxy-3'-fluorodine (0.50 g, 2.2 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE celluluse was added and the suspension was stirred at 45° C. After 3 days, 100 ml MeOH was added to the reaction mixture. The resulting mixture was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:acetone:methanol (97:2:1). Solvent was removed and lyophilization yielded 0.40 g of 2-amino-9-(2,3-dideoxy-3-fluoro-β-D-erythro-pentofuranosyl)-6-(4-methoxyanilino)-9H-purine (48%): mp 190°–191° C.; TLC $R_f$ 0.70 (silica gel, MeCN:15N $NH_4OH:H_2O/85:5:10$); $[\alpha]_D^{20}$ −10.6 (c=0.5, DMF); UV $\lambda_{max}$ ($\epsilon \times 10^{-3}$) at pH 7, 298 (17.7); at pH 13, 298 (17.7); $^1$H NMR (200 MHz, DMSO-d$_6$) δ9.30 (s, 1H, NH), 8.05 (s, 1H, H$_8$), 7.85 (d, 2H, J=9.0 Hz), 6.86 (d, 2H, J=9.0 Hz), 6.26 (dd, 1H, H$_{2'}$, J=9.4 Hz, J=5.6 Hz), 6.07 (s, 2H, NH$_2$), 5.42 (dd, 1H, H$_{3'}$, J=53.8 Hz, J=4.0 Hz), 5.43 (t, 1H, OH$_{,J}$=5.7 Hz), 4.25—4.35 (m, 1H, H$_{4'}$), 3.73 (s, 3H, OCH$_3$), 3.59–3.62 (m, 2H, H$_{5'}$ and H$_{5''}$), and 2.78–3.08 and 2.50–2.68 (m, 2H, H$_{2'}$ and H$_{2''}$); MS (ci) 375 (M+1), 355 (M-F), 257 (MH$_2$—C$_5$H$_8$FO$_2$).

Anal. ($C_{17}H_{19}FN_6O_3$·0.6$_2$O), C, H, F, N. Calculated (Found): C, 53.01 (52.98); H, 5.29 (4.94); F, 4.93 (4.75); N, 21.82 (21.46).

EXAMPLE 34

2-Amino-9-(2,3-dideoxy-3-fluoro-β-D-erythro-pentofuranosyl)-6-morpholino-9H-purine 2-Amino-6-morpholino-9H-purine was prepared by displacement of the chlorine group on 2-amino-6-chloropurine (Aldrich Chemical Company) by morpholine (Aldrich Chemical Company).

2-Amino-6-morpholino-9H-purine (0.58 g 2.6 moles) and 2',3'-dideoxy-3'-fluorouridine (0.50 g, 2.2 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added and the suspension was stirred at 45° C. After 8 days, 100 ml MeOH was added to the reaction mixture. The resulting mixture was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:methanol:acetone (96:2:2). Solvent was removed and lyophilization yielded 0.503 g of 2-amino-9-(2,3-dideoxy-3-fluoro-β-D-erythro-pentofuranosyl)-6-morpholino-9H-purine (68%): mp165°–167° C.; TLC $R_f$ 0.70 (silica gel, MeCN:15N $NH_4OH:H_2O/85:5:10$); $[\alpha]_D^{20}$ −16.4 (c=0.5, DMF); UV $\lambda_{max}$ ($\epsilon \times 10^{-3}$) at pH 7, 289 (16.6); at pH 13, 289 (16.5); $^1$H NMR (300 MHz, DMSO-d$_6$) δ7.97 (s, 1H, H$_8$), 6.22 (dd, 1H, H$_{1'}$, J=9.3 Hz, J=5.7 Hz), 5.93 (s, 2H, NH$_2$), 5.37 (t, 1H, OH$_{5'}$, J=5.5 Hz), 5.3–5.5 (m, 1H, H$_{3'}$), 4.0–4.23 (bm, 5H, H$_{4'}$ and morpholino ring), 3.63–3.66 (m, 4H, morpholino ring), 3.56 (t, 2H, H$_{5'}$ and H$_{5''}$, J=5.0 Hz), and 2.70–2.95 and 2.45–2.61 (m, 2H, H$_{2'}$ and H$_{2''}$); MS (ci) 339 (M+1), 319 (M-F),221 (MH$_2$—C$_5$H$_8$FO$_2$).

Anal. ($C_{14}H_{19}FN_6O_3$·0.2H$_2$O), C, H, F, N. Calculated (Found): C, 49.18 (49.05); H, 5.72 (5.35); F, 5.56 (5.32); N, 24.58 (24.19).

EXAMPLE 35

6-(Allylamino)-2-amino-9-(2,3-dideoxy-3-fluoro-β-D-erythro-pentofuranosyl)-9H-purine 6-(Allylamino)-2-amino-9H-purine was prepared by displacement of the chlorine group on 2-amino-6-chloropurine (Aldrich Chemical Company) by allylamine (Aldrich Chemical Company).

6-(Allylamino)-2-amino-9H-purine (0.51 g, 2.6 mmoles) and 2',3'-dideoxy-3'-fluorouridine (0.50 g, 2.2 mmoles) were suspended in 50 ml 10 mM potassium phosphate buffer, pH 7.0, containing 0.40% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added and the suspension was stirred at 45° C. After 7 days, 100 ml MeOH was added to the reaction mixture. The resulting mixture was applied to a column containing AG1-X2 (OH— form, 2.5×10 cm) and eluted with MeOH. Fractions containing were pooled, concentrated, and flash chromatographed on silica gel (2.5× 20 cm) with dichloromethane:acetone:methanol (96:2:2). Solvent was removed and lyophilization yielded 0.314 g of 6-(allylamino)-2-amino-9-(2,3-dideoxy-3-fluoro-β-D-erythro-pentofuranosyl)-9H-purine (46%): mp 128°–129° C.; TLC $R_f$ 0.70 (silica gel, MeCN:15N $NH_4OH:H_2O/85:5:10$); $[\alpha]_D^{20}$ −15.2 (c=0.5, DMF); UV $\lambda_{max}$ ($\epsilon \times 10^{-3}$) at pH 7, 281 (14.7); at pH 13, 281 (14.0); $^1$H NMR (300 MHz, DMSO-d$_6$) δ7.91 (s, 1H, H$_8$), 7.44–7.48 (b, 1H, NH), 6.20 (dd, 1H, H$_{1'}$, J=9.3 Hz, J=5.6 Hz), 5.82–5.95 (M, 3H), 5.51 (t, 1H, OH$_{5'}$, J=5.8 Hz), 5.38 (dd, 1H, H$_{3'}$, J=53.7 Hz, J=4.3 Hz), 5.03–5.14 (m, 2H), 4.25 (dt, 1H, H$_{4'}$, J=27.4 Hz, J=4.5 Hz), 4.0–5.05 (b, 2H, NCH$_2$), 3.57 (t, 2H, H$_{5'}$, and H$_{5''}$, J=5.0 Hz), and 2.75–3.00 and 2.45–2.62 (m, 2H, H$_{2'}$ and H$_{2''}$; MS (ci) 309 (M+1), 289 (M-F), 191 (MH$_2$—C$_5$H$_8$FO$_2$).

Anal. ($C_{13}H_{17}FN_6O_2$·0.15H$_2$O), C, H, F, N. Calculated (Found): C, 50.20 (49.94); H, 5.61 (5.41); F, 6.11 (6.14); N, 27.02 (26.69).

EXAMPLE 36

2-Amino-9-(2,3-dideoxy-3-fluoro-β-D-erythro-pentofuranosyl)-6-(hexahydroazepin-1-yl)-9H-purine 2-Amino-6-(hexahydroazepin-1-yl)-9H-purine was prepared by displacement of the chlorine group on 2-amino-6-chloropurine (Aldrich Chemical Company) by hexamethyleneimine (Aldrich Chemical Company).

2-Amino-6-hexahydroazepin-1-yl-9H-purine (0.60 g, 2.6 mmoles) and 2',3'-dideoxy-3'-fluorouridine (0.50 g, 2.2 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added and the suspension was stirred at 45° C. After 7 days, 100 ml MeOH was added to the reaction mixture. The resulting mixture was applied to a column containing AG1-X2 (OH— form, 2.5×10 cm) and eluted with MeOH. Fractions containing product were pooled, concentrated, and flash chromatographed on silica gel (2.5× 20 cm) with dichloromethane:acetone:methanol (97:2:1). Solvent was removed and lyophilization yielded 0.149 g of 2-amino-9-(2,3-dideoxy-3-fluoro-β-D-erythro-pentofuranosyl)-6-hexahydroazepin-1-yl)-9H-purine (19%): mp 110°–114° C.: TLC $R_f$ 0.70 (silica gel, MeCN:15N $NH_4OH:H_2O$/85:5:10); $[\alpha]_D^{20}$ −16.6 (c=0.5, DMF); UV $\lambda_{max}$ ($\epsilon \times 10^{-3}$) at pH 7, 285 (17.6); at pH 13, 285 (17.3); $^1H$ NMR (300 MHz, DMSO-$d_6$) δ7.92 (s, 1H, $H_8$), 6.21 (dd, 1H, $H_{1'}$, J=9.4 Hz, J=5.5 Hz), 5.72 (s, 2H, $NH_2$), 5.45–5.49 (m, 1H, $OH_{5'}$), 5.36 (dd, 1H, $H_{3'}$, J=53.7 Hz, J=4.3 Hz), 4.16 (dt, 1H, $H_{4'}$, J=27.2 Hz, J=4.4 Hz), 3.74–4.24 (b, 4H), 3.56 (t, 2H, $H_{5'}$ and $H_{5''}$, J=5.0 Hz), 2.75–2.95 and 2.40–2.60 (m, 2H, $H_{2'}$ and $H_{2''}$), and 1.65–1.80 and 1.40–1.55 (b, 8H); MS (ci 351 (M+1), 331 (M-F), 233 ($MH_2$—$C_5H_8FO_2$).

Anal. ($C_{16}H_{23}FN_6O_2 \cdot 0.15H_2O$), C, H, F, N. Calculated (Found): C, 54.43 (54.16); H, 6.65 (6.55); F, 5.38 (5.20); N, 23.80 (23.48).

EXAMPLE 37

2-Chloro-9-(2,3-dideoxy-3-fluoro-β-D-erythro-pentofuranosyl)-6-(methylamino)-9H-purine 2-Chloro-6-methylamino-9H-purine was prepared by displacement of the chlorine group on 2,6-dichloropurine (Aldrich Chemical Company) by methylamine (Aldrich Chemical Company).

2-Chloro-6-methylamino-9H-purine (0.48 g 2.6 moles) and 2',3'-dideoxy-3'-fluorouridine (0.50 g, 2.2 mmoles) were suspended in 50 ml 10 mM potassium phosphate buffer, pH 7.0, containing 0.04% potassium azide. Purine nucleoside phosphorylase (1120 I.U.). and thymidine phosphorylase (10,000 I.U.) (Krenitsky, et al., *Biochemistry*, 20, 3615, 1981 and U.S. Pat. No. 4,381,344) immobilized on DEAE cellulose was added and the suspension was stirred at 45° C. After 9 days, 100 ml MeOH was added to the reaction mixture. The resulting mixture was filtered through Celite. The filtrate was flash chromatographed on silica gel (2.5×20 cm) with dichloromethane:methanol (96:4). Solvent was removed and lyophilization yielded 0.117 g of 2-chloro-9-(2,3-dideoxy-3-fluoro-β-D-erythro-pentofuranosyl)-6-(methylamino)-9H-purine (18%): mp 181°–182° C.; TLC $R_f$ 0.70 (silica ge, MeCN:15N $NH_4OH:H_2O$/85:5:10); $[\alpha]_D^{20}$ −18.6 (c=0.5, DMF); UV $\lambda_{max}$ ($\epsilon \times 10^{-3}$) at pH 7, 269 (17.6); at pH 13, 269 (16.8); $^1H$ NMR (400 MHz, DMSO-$d_6$) δ8.35 (s, 1H, $H_8$), 8.32 (b, 1H, NH), 6.30 (dd, 1H, $H_{1'}$, J=9.1 Hz, J=5.7 Hz), 5.41 (dd, 1H, $H_{3'}$, J=53.5 Hz, J=4.1 Hz), 5.16 (t, 1H, $OH_{5'}$, J=5.7 Hz), 4.16–4.24 (m, 1H, $H_{4'}$), 3.57 (t, 2H, $H_{5'}$ and $H_{5''}$, J=5.2 Hz), 2.83–3.00 (m, 4H, $NCH_3$ and $H_{2'}$) and 2.60–2.73 (m, 1H, $H_{2''}$); MS (ci) 302 (M+1), 282 (M-F), 184 ($MH_2$—$C_5H_8FO_2$).

Anal. ($C_{11}H_{13}ClFN_5O_2$) C, H, Cl, F, N. Calculated (Found): C, 43.79 (43.94); H, 4.34 (4.38); Cl, 11.75 (11.87); F, 6.30 (6.19); N, 23.21 (22.84).

EXAMPLE 38

6-Cyclopropylmethoxy-9-(2,3-dideoxy-3-fluoro-β-D-erythro-pentofuranosyl)-9H-purine 6-Cyclopropylmethoxy-9H-purine was prepared by displacement of the chlorine group on 6-chloropurine (Aldrich Chemical Company) by cyclopropanemethanol (Aldrich Chemical Company) in the presence of sodium hydride.

6-Cyclopropylmethoxy-9H-purine (0.50 g, 2.6 mmoles) and 2',3'-dideoxy-3'-fluorouridine (0.50 g, 2.2 mmoles) were suspended in 40 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added to the reaction and the suspension was stirred at 45° C. After 6 days, 150 ml MeOH was added to the reaction. The reaction was applied to a column containing AG1-X2 (OH— form, 2.5×10 cm) and eluted with MeOH. Fractions containing product were pooled, concentrated, and flash chromatographed on silica gel (5×20 cm) with dichloromethane:acetone (9:1). Solvent was removed and lyophilization yielded 0.392 g of 6-cyclopropylmethoxy-9-(2,3-dideoxy-3-fluoro-β-D-erythro-pentofuranosyl)-9H-purine (58%): mp 100° C.; TLC $R_f$ 0.90 (silica gel, MeCN:15N $NH_4OH:H_2O$/ 85:5:10); $[\alpha]_D^{20}$ −18.8 (c=0.5, DMF); UV $\lambda_{max}$ ($\epsilon \times 10^{-3}$) at pH 7, 251 (12.5); at pH 13, 149.5 (12.1); $^1H$ NMR (400 MHz, DMSO-$d_6$) δ8.59 and 8.50 (2s, 2H, $H_2$ and $H_8$), 6.46 (dd, 1H, $H_{1'}$, J=9.1 Hz, J=5.7 Hz), 5.44 (dd, 1H, $H_{3'}$, J=53.5 Hz, J=4.4 Hz), 5.23 (t, 1H, $OH_{5'}$, J=5.6 Hz), 4.37 (d, 2H, $OCH_2$, J=7.4 Hz), 4.18–4.29 (m, 1H, $H_{4'}$), 3.57–3.60 (m, 2H, $H_{5'}$ and $H_{5''}$), 2.92–3.10 and 2.65–2.75 (2m, 2H, $H_{2'}$ and $H_{2''}$), and 1.25–1.35, 0.55–0.60, and 0.36–0.40 (3m, 5H, cyclopropyl); MS (ci)309 (M+1), 289 (M-F), 191 ($MH_2$—$C_5H_8FO_2$).

Anal. ($C_{14}H_{17}FN_4O_3$) C, H, F, N. Calculated (Found): C, 54.54 (54.28); H, 5.56 (5.37); F, 6.16 (5.94); N, 18.17 (17.94).

EXAMPLE 39

2-Amino-9-(2,3-dideoxy-3-fluoro-β-D-erythro-pentofuranosyl)-6-((2-hydroxyethyl)amino)-9H-purine 2-Amino-6-((2-hydroxyethyl)amino)-9H-purine was prepared by displacement of the chlorine group on 2-amino-6-chloropurine (Aldrich Chemical Company, Milwaukee, Wis.) by β-ethanolamine (Aldrich Chemical Company, Milwaukee, Wis.).

2-Amino-6-((2-hydroxyethyl)amino)-9H-purine (0.55 g, 2.6 mmoles) and 2',3'-dideoxy-3'-fluorouridine (0.50 g, 2.2 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added and the suspension was stirred at 45° C. After 18 days, 150 ml MeOH was added to the reaction mixture. The resulting mixture was applied to a column containing AG1-X2 (OH— form, 2.5×10 cm) and eluted with MeOH. Fractions containing product were pooled, concentrated, and flash chromatographed on silica gel 2.5×20 cm) with dichloromethane:methanol:acetone (96:2:2). Solvent was removed and lyophilization yielded 0.14 g of 2-amino-9-(2,3-dideoxy-3-fluoro-β-D-erythro-pentofuranosyl)-6-((2-hydroxyethyl)amino-9H-purine (19%): mp 144° C.; $[\alpha]_D^{20}$ −29.4° C. (c=0.5, DMF); UV $\lambda_{max}$ ($\epsilon \times 10^{-3}$) at pH 7, 282 (12.0); at pH 13, 281 (13.213.9); $^1H$ NMR (300 MHz, DMSO-$d_6$) δ7.93 (s, 1H, $H_8$), 7.14 (b, 1H, NH), 6.21 (dd, 1H, $H_{1'}$, J=9.4 Hz, J=5.6 Hz), 5.85 (bs, 2H, $NH_2$), 5.30–5.35 (m, 2H, $OH_{5'}$ and $H_{3'}$), 4.74 (b, 1H, OH), 4.18 (dt, 1H, $H_{4'}$, J=27.1 Hz, J=4.4 Hz), 3.42–3.62 (b, 6H, H, $H_{5'}$,$H_{5''}$, $NCH_2CH_2O$), 2.76–3.01 and 2.49–2.63 (m, 2H, $H_{2'}$ and $H_{2''}$); MS (ci) 313 (M+1), 293 (M-F), 195 ($MH_2$—$C_5H_8FO_2$).

Anal. ($C_{12}H_{17}FN_6O_3 \cdot 0.6H_2O$), C, H, F, N. Calculated (Found): C, 44.61 (44.64); H, 5.68 (5.39); F, 5.88 (5.70); N, 26.01 (25.64).

EXAMPLE 40

2-Amino-6-chloro-9-(2,3-dideoxy-3-fluoro-β-D-erythro-pentofuranosyl)-9H-purine

2-Amino-6-chloro-9H-purine (0.48 g, 2.8 mmoles), (Aldrich Chemical Company, Milwaukee, Wis.) and 2',3'-dideoxy-3'-fluorouridine (0.50 g, 2.2 mmoles) were suspended in 50 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added and the suspension was stirred at 45° C. After 2 days, the reaction mixture was filtered and solvent was removed in vacuo. The residue was flash chromatographed on silica gel (2.5×20 cm) with dichloromethane:methanol:acetone (96:2:2). Solvent was removed and lyophilization yielded 0.15 g of 2-amino-6-chloro-9-(2,3-dideoxy-3-fluoro-β-D-erythro-pentofuranosyl)-purine (23%): mp 172° C.; $[\alpha]_D^{20}$ −41.0 (c=0.5, DMF); UV $\lambda_{max}$ (ε×10$^{-3}$) at pH 7, 308 (7.7); at pH 13, 303 (7.6); $^1$H NMR (300 MHz, DMSO-d$_6$) δ8.36 (s, 1H, H$_8$), 7.01 (s, 2H, NH$_2$), 6.27 (dd, 1H, H$_{1'}$, J=9.0 Hz, J=5.8 Hz), 5.42 (dd, 1H, H$_{3'}$, J=53.8 HZ, J=4.4 Hz), 5.14 (t, 1H, OH$_{5'}$, J=5.4 Hz), 4.20 (dt, 1H, H$_{4'}$, J=26.5 Hz, J=4.8 Hz), 3.57 (t, 2H, H$_{5'}$ and H$_{5''}$, J=5.3 Hz), 2.63–3.04 (m, 2H, H$_{2'}$ and H$_{2''}$); MS (ci) 288 (M+1), 268 (M-F), 70 (MH$_2$—C$_5$H$_8$FO$_2$).

Anal. (C$_{10}$H$_{11}$ClF$_5$O$_2$.0.25H$_2$O), C, H, F, N. Calculated (Found): C, 41.11 (41.22); H, 3.97 (3.80); Cl, 12.13 (12.14); N, 23.97 (23.75).

EXAMPLE 41

2-Amino-9-(2,3-dideoxy-3-fluoro-β-D-erythro-pentofuranosyl)-6-methylamino-9H-purine 2-Amino-6-methylamino-9H-purine was prepared by displacement of the chloring group on 2-amino-6-chloropurine (Aldrich Chemical Company, Milwaukee, Wis.) by methylamine (Aldrich Chemical Company, Milwaukee, Wis.).

2-Amino-6-methylamino-9H-purine (0.43 g, 2.6 mmoles) and 2',3'-dideoxy-3'-fluorouridine (0.50 g, 2.2 mmoles) were suspended in 40 ml 10 mM potassium phosphate buffer, pH 7.0, containing 0.04% potassium azide. Purine nucleoside phosphorylase (1120 I.U.) and thymidine phosphorylase (10,000 I.U.) (Krenitsky, et al., *Biochemistry*, 20, 3615, 1981 and U.S. Pat. No. 4,381,344) immobilized on DEAE cellulose was added and the suspension was stirred at 45° C. After 2 days, 100 m, MeOH was added to the reaction mixture. The resulting mixture was applied to a column containing AG1-X2 (OH$^-$ form, 2.5×10 cm) and eluted with MeOH. Fractions containing product were pooled, concentrated, and flash chromatographed on silica gel (2.5× 20 cm) with dichloromethane:methanol (96:4). Solvent was removed and lyophilization yielded 0.35 g of 2-amino-9-(2,3-dideoxy-3-fluoro-β-D-erythro-pentofuranosyl)-6-methylamino-9H-purine (56%): mp 111° C.; TLC R$_f$O. (silica gel, MeCN:15N NH$_4$OH:H$_2$O/85:5:10); $[\alpha]_D^{20}$ −30.0 (c=0.5, DMF); UV $\lambda_{max}$ (ε×10$^{-3}$) at pH 7, 280 (13.2); at pH 13, 280 (13.2); $^1$H NMR (300 MHz, DMSO-d$_6$) δ7.91 (s, 1H, H$_8$), 7.30 (b, 1H, NH), 6.22 (dd, 1H, H$_{1'}$, J=9.4 Hz, J=5.5 Hz), 5.85 (bs, 2H, NH$_2$), 5.55 (t, 1H, OH$_{5'}$, J=5.3 Hz), 5.40 (dd, 1H, H$_{3'}$, J=53.7 Hz, J=4.0 Hz), 4.19 (dm, 1H, H$_{4'}$, J=27.5 Hz), 3.59 (t, 2H, H$_{5'}$ and H$_{5''}$, J=4.6 Hz), 2.82–2.96 and 2.50–2.61 (m, 5H, NCH$_3$, H$_{2'}$ and $_{2''}$); MS (ci) 283 (M+1), 263 (M-F), 165 (MH$_2$—C$_5$H$_8$FO$_2$).

Anal. (C$_{11}$H$_{15}$FN$_6$O$_2$.0.4H$_2$O) C, H, F, N. Calculated (Found): C, 45.64 (45.74); H, 5.50 (5.30); F, 6.56 (6.27); N, 29.03 (28.82).

EXAMPLE 42

Tablet Formulations

The following formulations A, B and C are prepared by wet granulation of the ingredients with a solution of povidone, followed by addition of the magnesium separate and compression.

Formulation A

|     |                         | mg/tablet | mg/tablet |
|-----|-------------------------|-----------|-----------|
| (a) | Active ingredient       | 250       | 250       |
| (b) | Lactose B.P.            | 210       | 26        |
| (c) | Povidone B.P.           | 15        | 9         |
| (d) | Sodium Starch Glycollate| 20        | 12        |
| (e) | Magnesium Stearate      | 5         | 3         |
|     |                         | 500       | 300       |

Formulation B

|     |                         | mg/tablet | mg/tablet |
|-----|-------------------------|-----------|-----------|
| (a) | Active ingredient       | 250       | 250       |
| (b) | Lactose                 | 150       | —         |
| (a) | Avicel PH 101           | 60        | 26        |
| (d) | Povidone B.P.           | 15        | 9         |
| (e) | Sodium Starch Glycollate| 20        | 12        |
| (f) | Magnesium Stearate      | 5         | 3         |
|     |                         | 500       | 300       |

Formulation C

|                    | mg/tablet |
|--------------------|-----------|
| Active ingredient  | 100       |
| Lactose            | 200       |
| Starch             | 50        |
| Povidone           | 5         |
| Magnesium stearate | 4         |
|                    | 359       |

The following formulations, D and E, are prepared by direct compression of the admixed ingredients.

Formulation D

|                          | mg/capsule |
|--------------------------|------------|
| Active Ingredient        | 250        |
| Pregelatinised Starch NF15 | 150      |
|                          | 400        |

Formulation E

|                   | mg/capsule |
|-------------------|------------|
| Active Ingredient | 250        |
| Lactose           | 150        |
| Avicel            | 100        |
|                   | 500        |

Formulation F (Controlled Release Formulation)

The formulation is prepared by wet granulation of the following ingredients with a solution of povidone followed by addition of the magnesium stearate and compression.

|     |                                                    | mg/tablet |
| --- | -------------------------------------------------- | --------- |
| (a) | Active Ingredient                                  | 500       |
| (b) | Hydroxypropylmethylcellulose (Methocel K4M Premium)| 112       |
| (c) | Lactose B.P.                                       | 53        |
| (d) | Povidone B.P.C.                                    | 28        |
| (e) | Magnesium Stearate                                 | 7         |
|     |                                                    | 700       |

Drug release takes place over a period of about 6–8 hours and is complete after 12 hours.

EXAMPLE 43

Capsule Formulations

Formulation A

A capsule formulation is prepared by admixing the ingredients of Formulation D in Example 3 above and filling into two-part hard gelatin capsule.

Formulation B

|     |                         | mg/capsule |
| --- | ----------------------- | ---------- |
| (a) | Active ingredient       | 250        |
| (b) | Lactose B.P.            | 143        |
| (c) | Sodium Starch Glycollate| 25         |
| (d) | Magnesium Stearate      | 2          |
|     |                         | 420        |

Capsules are prepared by admixing the above ingredients and filling into two-part hard gelatin capsules.

Formulation C

|     |                   | mg/capsule |
| --- | ----------------- | ---------- |
| (a) | Active ingredient | 250        |
| (b) | Macrogol 4000 BP  | 350        |
|     |                   | 600        |

Capsules are prepared by melting the Macrogol 4000 BP, dispersing the active ingredient in the melt and filling the melt into two-part hard gelatin capsules.

Formulation D

|                   | mg/capsule |
| ----------------- | ---------- |
| Active ingredient | 250        |
| Lecithin          | 100        |
| Arachis Oil       | 100        |
|                   | 450        |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extrudate and drying. The dried pellets are then coated with the release-controlling membrane (d) and filled into two-piece, hard gelatin capsules.

|     |                          | mg/capsule |
| --- | ------------------------ | ---------- |
| (a) | Active Ingredient        | 250        |
| (b) | Microcrystalline Cellulose| 125       |
| (c) | Lactose BP               | 125        |
| (d) | Ethyl Cellulose          | 13         |
|     |                          | 513        |

EXAMPLE 44

Injectable Formulation

Formulation A

| Active ingredient             | 0.200 g                |
| ----------------------------- | ---------------------- |
| Hydrochloric acid solution, 0.1 M | q.s. to pH 4.0 to 7.0 |
| Sodium hydroxide solution, 0.1 M  | q.s. to pH 4.0 to 7.0 |
| Sterile water                 | q.s. to 10 ml          |

The active ingredient is dissolved in most of the water (35°–40° C.) and the pH adjusted to between 4.0 and 7.0 using the hydrochloride acid or the sodium hydroxide as appropriate. The batch is then made up to volume with the water and filtered through a sterile micropore filter into a sterile amber glass vial 10 ml and sealed with sterile closures and overseals.

Formulation B

| Active ingredient | 0.125 g |
| ----------------- | ------- |
| Sterile, pyrogen-free, pH 7 phosphate buffer, | q.s. to 25 ml |

EXAMPLE 45

Intramuscular Injection

| Active Ingredient         | 0.20 g  |
| ------------------------- | ------- |
| Benzyl Alcohol            | 0.10 g  |
| Glycofurol 75             | 1.45 g  |
| Water for Injection  q.s. to. | 3.00 ml |

The active ingredient is dissolved in the glycofurol. The benzyl alcohol is then added and dissolved, and water added to 3 ml. The mixture is then filtered through a sterile micropore filter and sealed in sterile amber glass vials 3 ml.

EXAMPLE 46

Syrup

| Active ingredient          | 0.25 g     |
| -------------------------- | ---------- |
| Sorbitol Solution          | 0.10 g     |
| Glycerol                   | 2.00 g     |
| Sodium Benzoate            | 0.005 g    |
| Flavour, Peach 17.42.3169  | 0.0125 ml  |
| Purified Water  q.s. to    | 5.00 ml    |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

EXAMPLE 47

Suppository

|  | mg/suppository |
|---|---|
| Active Ingredient | 250 |
| Hard Fat, BP (Witepsol H15 - Dynamit Nobel) | 1770 |
|  | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.0 g of the mixture is filled into suitable, 2 ml plastic moulds. The suppositories are allowed to cool to room temperature.

EXAMPLE 48

Pessaries

|  | mg/pessary |
|---|---|
| Active ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

EXAMPLE 49

Antiviral testing a) Antiviral Activity Against Human Immunodeficiency Virus (HIV).

Anti-HIV activity of compounds of formula (I) was determined using the method of Averett D. R., 1989, J. Virol. Methods, 23, pp263–276, by measuring the ability of the compound to reverse the cytopathic effect of HIV infection. This was determined by a quantitative assessment of cell growth monitored at the fifth day post infection by a propidium iodide dye uptake test. MT4 cells were incubated with $100 \times TCID_{50}$ of HIV-1 (strain 3B) or HIV-2 (Zagury strain) for one hour prior to addition of the compound in six different concentrations varying from 2 to 200 μM. The cells were allowed to incubate for five days at 37° C. On day 5, NP-40, a detergent, was added to a final concentration of 0.5% immediately prior to analysis. Cell number was determined using a method which measures the fluorescence of a dye (propidium iodide) which binds to DNA. Since the amount of DNA is directly proportional to cell number, this fluorescence assay is an indication of cell growth. While uninfected cells double in cell number several times during the five days duration of the assay, HIV-infected cells grow very little, if at all. A compound which reverses the cytopathic effect of HIV would allow for rapid cell growth, approaching that of the mock-infected cells.

The antiviral effect of a drug is reported as an $IC_{50}$, i.e. as the inhibitory concentration that would protect 50% of the cells from cell killing, measured as 50% of that cell growth determined for uninfected MT4 cell controls.

| Example | $IC_{50}$ HIV |
|---|---|
| 2-Amino-9-(2,3-dideoxy-3-fluoro-β-D-erythro-pentofuranosyl)-6-(dimethylamino)-9H-purine | 8 μM | b) Antiviral Activity Against Hepatitis B Virus (HBV)

Anti-HBV activity of compounds of formula (I) was determined using a method described by Korba B. E. and Milman G., Antiviral Research, 1991, Vol.15, pp217–228.

The assay utilises the human HBV producer cell line of HepG2, 2.2.15, described and characterized by Sells et al., PNAS 84, 1005 (1987) and J. Virol. 62, 2836 (1988), has been shown to share many characteristics of the HBV chronically infected hepatocyte. It is infectious as demonstrated by the ability to cause disease in chimpanzees. This cell line was utilized in vitro to identify compounds with anti-HBV activity.

To test compounds for antiviral activity, monolayer cultures were treated with the compound (50–200 μM), for 9 days. Supernatant media containing extracellular virion DNA (Dane particles) were harvested on days 0, 4 and 9, treated with proteinase K (1 mg/mL) and sodium dodecyl sulfate (1%), and incubated at 50° C. for one hour. DNA was extracted with equal volumes of phenol followed by chloroform and then precipitated using ammonium acetate and propanol. The DNA precipitate was dissolved and collected on nitrocellulose using the procedure of Schleicher and Schuell (S & S, 10 Optical Ave., Keene, N.H. 03431, Publication 700, 1987), and treated as described by Southern in J. Mol. Biol. 98, 503 (1975). Cells were harvested and the intracellular DNA obtained after cell lysis with guanidine isothiocyanate. The intracellular DNA was handled in the same manner as the extracellular DNA. After precipitation by ammonium acetate and propanol, the intracellular DNA precipitate was dissolved, cut by restriction endonuclease, Hind III, applied co agarose gel and then treated as described by Southern to determine the quantity of replicative intermediate forms. The antiviral effect of the drug was determined by measuring at least a 100-fold reduction in the amount of Dane particles extruded into the culture medium and a similar decrease in the intracellular replicative intermediates.

|  | Extracellular HBV DNA (pg/ml, Culture Medium) | | |
|---|---|---|---|
|  | Day 0 | Day 4 | Day 9 |
| Untreated Cells | 59 | 75 | 94 |
|  | 47 | 64 | 88 |
|  | 65 | 100 | 71 |
| Treated Example 13 (25 μm) | 77 | 65 | 110 |
|  | 60 | 57 | 9 |
|  | 99 | 33 | 3 |
|  | 77 | 53 | 6 |
|  | 67 | 51 | 2 |

We claim:
1. A compound of formula (I)

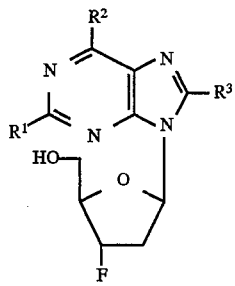

wherein:

$R^1$ is amino;

$R^2$ represents

—$NR^4R^5$ wherein $R^4$ and $R^5$ together with the N atom to which they are attached form a 4-membered heterocyclic ring, which ring is bonded to the purine base via the nitrogen atom or —$OR^8$ wherein $R^8$ represents $C_{3-6}$ cycloalkyl $C_{1-3}$ alkyl or $C_{6-10}$ aryl $C_{1-3}$ alkyl and $R^3$ is hydrogen;

$R^3$ is hydrogen, amino, halogen or $C_{1-6}$ alkyl; or a physiologically functional derivative thereof.

2. A compound according to claim 1 selected from:

2-amino-6-benzyloxy-9-(2,3-dideoxy-3-fluoro-β-D-erythro-pentofuranosyl)-9H-purine;

2-amino-6-azetidinyl-9-(2,3-dideoxy-3-fluoro-β-D-erythro-pentofuranosyl)-9H-purine; and physiologically functional derivatives thereof.

3. A physiologically functional derivative of a compound according to claim 1 or 2.

4. A derivative according to claim 3 selected from carboxylic acid esters, sulphonate esters, amino acid esters, mono-, di- or triphosphate esters and salts.

5. A pharmaceutical formulation comprising a compound according to claim 1, together with a pharmaceutically acceptable carrier therefore.

6. A formulation according to claim 5 in unit dosage form.

7. A formulation according to claim 6 in the form of a tablet or capsule.

8. A pharmaceutical formulation comprising the compound of claim 2 together with a pharmaceutically acceptable carrier therefore.

9. A method for treating an HBV or HIV infection in an infected animal which comprises administering to said animal a therapeutically effective amount of a compound of any one of claims 4–7.

10. A method according to claim 9 wherein said therapeutically effective amount is from 0.5 to 120 mg per kg body weight per day.

11. A method according to claim 9 wherein said effective amount is 2 to 6 mg per kg body weight per day.

* * * * *

UNITED STATES PATENT AND TRADEMARK OFFICE
CERTIFICATE OF CORRECTION

PATENT NO. : 5,663,154
DATED : September 2, 1997
INVENTOR(S) : Burns et al.

It is certified that error appears in the above-identified patent and that said Letters Patent is hereby corrected as shown below:

In claim 9, delete line 22 that reads: " one of claims 4-7."
Please insert -- one of claims 1-4. --

Signed and Sealed this

Twenty-fourth Day of March, 1998

Attest:

BRUCE LEHMAN

*Attesting Officer*     *Commissioner of Patents and Trademarks*